United States Patent [19]

Lloyd et al.

[11] Patent Number: 5,469,750
[45] Date of Patent: Nov. 28, 1995

[54] METHOD AND APPARATUS FOR SENSING FLOW IN TWO DIRECTIONS AND AUTOMATIC CALIBRATION THEREOF

[75] Inventors: Peter M. Lloyd, Oakland; Carl Ritson, San Jose; Eric T. Johansson, Dublin; Reid M. Rubsamen, Berkeley, all of Calif.

[73] Assignee: Aradigm Corporation, Hayward, Calif.

[21] Appl. No.: 10,772

[22] Filed: Jan. 29, 1993

Related U.S. Application Data

[63] Continuation-in-part of Ser. No. 664,758, Mar. 5, 1991, Pat. No. 5,404,871.

[51] Int. Cl.⁶ .............................. G01F 25/00; G01F 1/42
[52] U.S. Cl. .............................. 73/861.61; 73/3
[58] Field of Search .............. 73/3, 170.12, 170.14, 73/861.52, 861.53, 861.61, 861.63; 128/725

[56] References Cited

U.S. PATENT DOCUMENTS

| | | | |
|---|---|---|---|
| 2,255,771 | 9/1941 | Golay | 73/170.12 |
| 3,435,676 | 4/1969 | Brockner et al. | 73/170.12 |
| 3,735,752 | 5/1973 | Rodder . | |
| 4,083,245 | 4/1978 | Osborn | 73/861.53 |
| 4,848,163 | 7/1989 | Vacirca | 73/861.63 |
| 4,884,460 | 12/1989 | Nowacki et al. . | |
| 4,926,678 | 5/1990 | Pegrman | 73/3 |
| 4,932,269 | 6/1990 | Cammarata et al. | 73/861.61 |
| 4,965,756 | 10/1990 | Pearman et al. | 73/3 |
| 5,076,093 | 12/1991 | Jones, Jr. et al. | 73/3 |
| 5,201,322 | 4/1993 | Henry et al. | 73/861.61 |

FOREIGN PATENT DOCUMENTS

3709776A1  10/1988  Germany .

Primary Examiner—Richard Chilcot
Assistant Examiner—Harshad Patel
Attorney, Agent, or Firm—Karl Bozicevic; Fish & Richardson

[57] ABSTRACT

A method of calibrating the output of a transducer in a flow path through which a medication is delivered from a hand-held metered dose inhaler is disclosed. The transducer senses flow rates of human breath during inhalation and exhalation through a portion of a flow path in the inhaler. The flow rates have two non-linear flow characteristics in opposite directions. The flow path portion provides flow rate measurements representative of flow paths of the entire system. The method makes it possible to precisely calibrate so that precise doses of medication can be repeatedly delivered to a patient by inhalation.

5 Claims, 16 Drawing Sheets

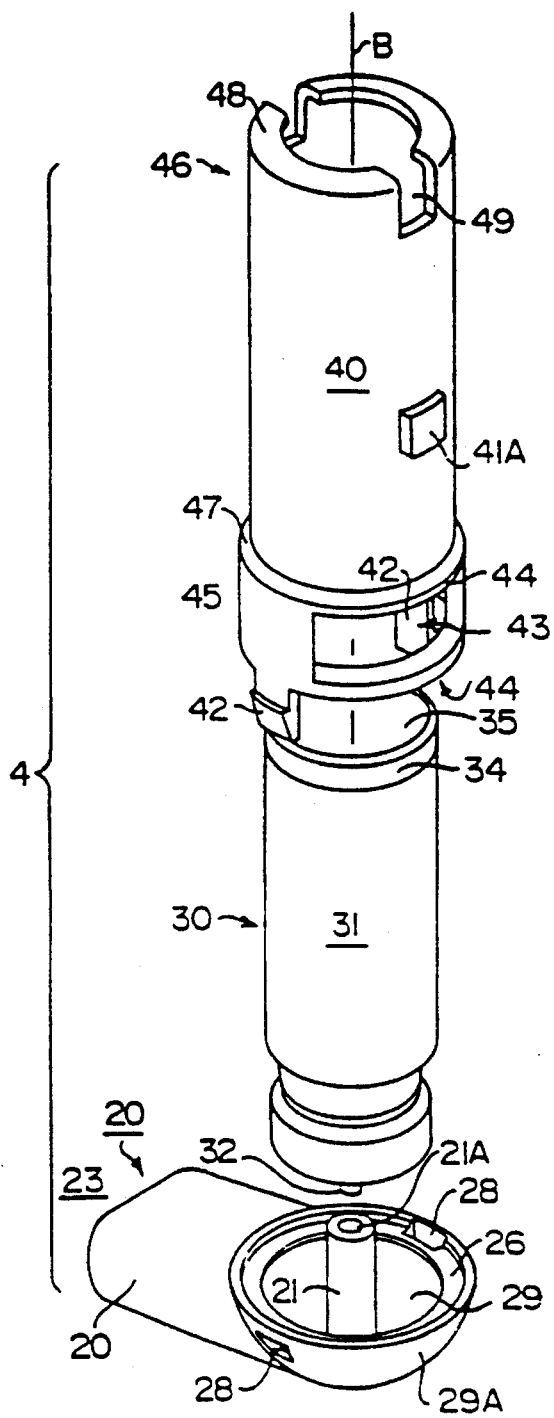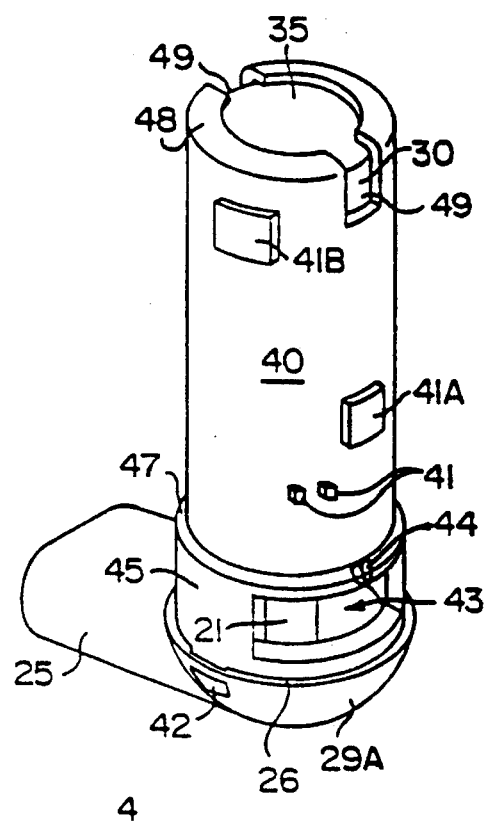
FIG. 5
FIG. 4

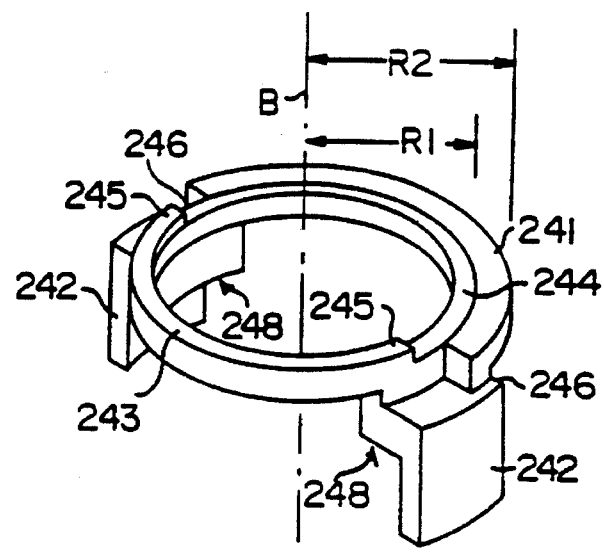
FIG. 15
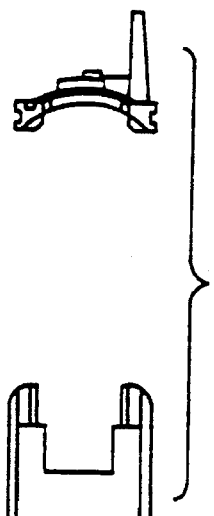
FIG. 16H
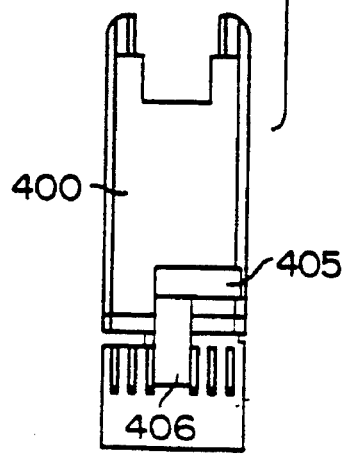

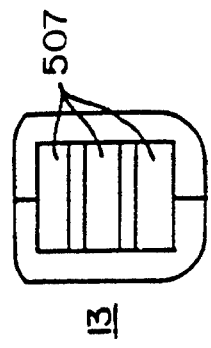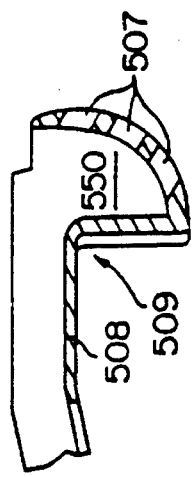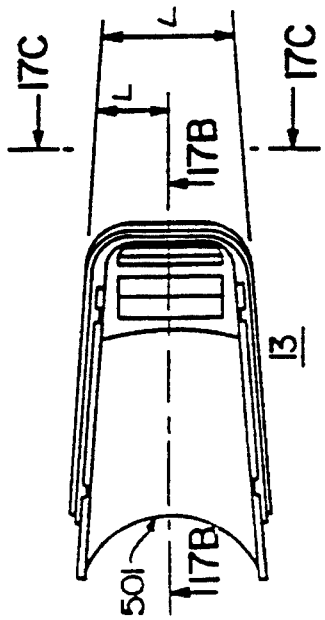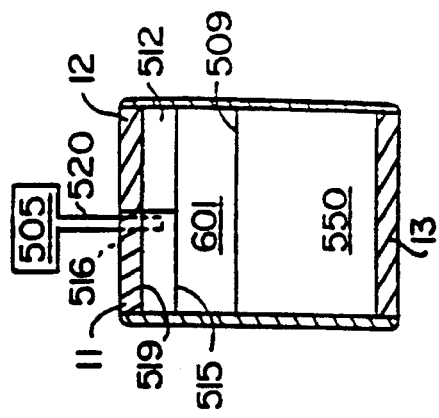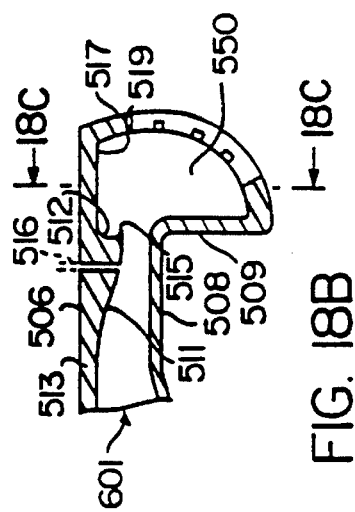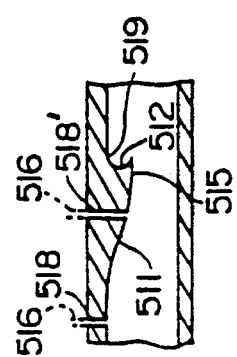

METHOD AND APPARATUS FOR SENSING FLOW IN TWO DIRECTIONS AND AUTOMATIC CALIBRATION THEREOF

RELATED APPLICATIONS

This application is a continuation-in-part of commonly assigned U.S. patent application Ser. No. 07/664,758, filed Mar. 5, 1991, now U.S. Pat. No. 5,404,871, issued Apr. 11, 1995 in the names of David E. Goodman and Reid M. Rubsamen and entitled DELIVERY OF AEROSOL MEDICATIONS FOR INSPIRATION.

This invention relates to improvements in the automatic delivery of aerosolized compounds and medications for inspiration by patients, more particularly to a durable electronically controlled breath actuated metered dose inhaler device having replaceable medication cassettes.

BACKGROUND OF THE INVENTION

Known devices for delivering aerosol medication for inhalation by a patient include metered dose inhalers that are manually operated and breath actuated. Breath actuated inhalers typically provide a metered dose automatically when the patient's inspiratory effort either moves a mechanical lever or the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978; 4,896,832; a product available from 3M Healthcare known as Aerosol Sheathed Actuator and Cap; and a product available from Riker Laboratories known as Autohaler. As used herein, references to "effort" and to "flow" are to the movement of air into and out of the patient's pulmonary system. The flow is typically detected as a flow rate (1/min), a flow volume (1), or a combination of a flow rate and flow volume or more than one flow rate and/or more than one flow volume.

A major problem with manual metered dose inhalers is that the patient frequently actuates the device at the incorrect time during inspiratory flow, without inhaling, or during expiration and thus does not obtain the benefits of the intended drug therapy. Accordingly, patients may inspire too little medication, or take a second dose and receive too much medication.

One problem with breath activated drug delivery is that the dose is triggered on crossing a fixed threshold inspiratory effort. Thus, an inspiration effort may be sufficient to release a metered dose, but the inspiratory flow following the release may not be sufficient to cause the aerosol medication to pass into the desired portion of the patient's airways. Another problem exists with patients whose inspiratory effort is not sufficient to rise above the threshold to trigger the release valve at all either all of the time or some of the time. This leads to frustration and ineffective therapy.

The known metered dose inhalers include a canister and a body. The canister contains a reservoir of medication and aerosol propellant under pressure, a metering valve which includes a fixed size chamber that captures a defined and uniform volume of material, and a valve stem which operates to release a metered dose. The metering chamber is typically maintained open to the reservoir. To release a dose, the valve stem is pushed into the metering valve. This causes the metering valve, in sequence, to close the chamber relative to the reservoir and capture a fixed volume of material under pressure, to open the chamber relative to the valve stem to release the captured amount of material out a flowpath in the valve stem, to close the chamber relative to the valve stem, and then to open the chamber to the reservoir so that the chamber is positively refilled with medication/ aerosol blend under pressure, providing the next dose to be administered.

The metered dose inhaler body contains a receptacle for the canister and a valve actuator (also referred to as a valve stem receptacle) that contains a flow path which terminates in a nozzle and receives the valve stem in alignment with the flow path. The nozzle is typically at an angle to the flow path and directs the released aerosol into the patients' mouth (or nostril). The valve stem receptacle is typically passive. Thus, when the canister is pressed relative to the valve stem receptacle, by manual or automatic advance, the valve stem is pressed into the metering valve and causes the metered dose to be released through the flow paths in the valve stem and the valve stem receptacle and out the nozzle. Typically, the valve stem receptacle has a frictional fit with the valve stem so that the canister is thereby secured to the body.

One problem with conventional pressurized meter dose canister devices is that the metering chamber must be maintained open to the atmosphere for a period of time sufficient to release the entire dosage from the chamber. The required time period is a function of the interior dimensions of the valve stem, the valve stem receptacle, and the nozzle. Consequently, commercial manual metered dose inhalers are limited to valves and medication formulations having release times less than about a tenth of a second. This is so the patient is not burdened with having to control the valve release time in addition to synchronizing the release of medication with inspiration.

Metered dose inhalers also must be sufficiently agitated in order to obtain a homogeneous mixture of the medication and propellant blend for refilling the metering chamber following administration of a dose. A problem with some breath actuated metered dose inhalers is that their operating sequence leaves the metering chamber open to the valve stem and the atmosphere and closed to the reservoir, rather than vice versa. Accordingly, the patient must reset or cock the inhaler to fill the metering chamber with a dose. If this occurs a period of time after release of the last dose, or without sufficiently agitating the device prior to cocking, a non homogeneous mixture of medication and propellant may be loaded into the metering chamber. This results in more or less medication being delivered to the patient than intended.

Another problem with existing metered dose inhalers, whether or not breath actuated, is that the canisters and valve stem receptacles are factory preset to deliver a fixed dose in a relatively short period of time. This results in a given particle size distribution. That distribution may not, however, provide a maximum or optional desired respirable fraction of the aerosol mist that is suitable for a desired location of delivery of the medication in the particular patient. The known devices which attempt to solve this problem process the aerosol after it is generated and thus are inefficient and wasteful. See, e.g., U.S. Pat. No. 4,790,305, U.S. Pat. No. 4,926,852, U.S. Pat. No. 4,677,975 and U.S. Pat. No. 3,658,059.

A problem with breath actuated metered dose inhalers that are electronically controlled is that the actuators for pressing the metered dose canister consume considerable amounts of electrical power to deliver the force required to release a dose. Accordingly, they are not practical for use as battery operated devices. See, for example, Newman et al., *Thorax,* 1981, 36:52–55; Newman et al., *Thorax,* 1980, 35:234; Newman et al., *Eur. J. Respir. Dis.,* 1981, 62:3–21; and Newman et al., *Am. Rev. Respir. Dis.*, 1981, 124:317–320 (the "Newman references").

It is well known that pulmonary functions, such as forced expiratory volume in one second, forced vital capacity, and peak expiratory flow rate, can be measured based on measured flow rates and used both to diagnose the existence of medical conditions, to prescribe medication, and to ascertain the efficiency of a drug therapy program. See, for example, U.S. Pat. Nos. 3,991,304 and 4,852,582 and the Newman references. Heretofore, these tests have been performed using available spirometers. U.S. Pat. No. 4,852,582 also refers to using a peak flow rate meter to measure changes in peak flow rate before and after administration of a bronchodilator. The results of such tests before and after administration of several different medications are used to evaluate the efficacy of the medications.

A problem with the foregoing pulmonary function test devices is that they are complicated. Another problem is that the test data must be examined and interpreted by a trained medical practitioner to be meaningful. Another problem is that they do not provide adequately for altering the dosage of the medication administered in a single patient during the course of therapy, or from patient to patient, using the same delivery device for generating an aerosol of the same or different medications.

Another problem with the known techniques is that they do not meet the needs for a portable device that is hand held, battery powered, and measures flow in two directions such that each direction has a different range of flow values with good resolution in each range.

SUMMARY OF THE INVENTION

The present invention relates to improvements on the basic inventions set forth in U.S. application Ser. No. 07/664,758, the disclosure of which is incorporated herein by reference in its entirety. It is an object of this invention to provide improved apparatus, systems, and methods for delivering aerosol compounds for inspiration by a patient.

It is another object of this invention to provide improved apparatus, systems, and methods for delivering for inspiration an aerosol having a particle size distribution favorable for selective deposition into desired locations in a patient's pulmonary system.

It is another object to release a controlled amount of aerosol during a controllable and selectable time period, including a relatively slow release, to produce a metered dose having a selected particle size distribution and/or airway deposition location. It is another object to provide a mechanism for releasing fully a metered dose over a selected time period. It is another object to maintain open the metering chamber of a metered dose inhaler for a selectable period of time sufficient to release the full metered dose, and for refilling the metering valve immediately following release. It is another object to provide a release mechanism that can be programmed for a specific metering valve-nozzle emptying time. It is another object to deliver a metered dose of medication/propellent blend formulation having a slow release time.

It is another object of the invention to release automatically a controlled amount of medication when the patient's detected inspiratory flow exceeds a preselected or predetermined delivery threshold, and, if the detected flow does not exceed (or satisfy) the provided delivery threshold, to determine a new delivery threshold based on a detected flow parameter of the detected inspiratory flow not exceeding the prior delivery threshold, and to release a controlled amount of medication over a controllable time period when a subsequently detected flow exceeds the new determined delivery threshold. The determined threshold is thus recursively determined for each detected inspiratory flow not exceeding the previously established delivery threshold, whether that threshold is an initial preselected default triggering threshold, an initial predetermined delivery threshold based on a calibration breath, or a subsequently determined threshold.

It is another object of this invention to provide an improved flow transducer for measuring breath flow both for sensing inspiration to deliver aerosolized material for inspiration by a patient, and for sensing inspiration, expiration, and inspiratory and expiratory pauses for measuring a patient's pulmonary function. It is another object to provide variously for one or more of (1) varying the dosage or controlled amount of the aerosolized compound delivered for inspiration by the patient in response to detected changes in the patient's pulmonary function during a course of therapy directed to improving pulmonary function, (2) providing an acuity display of the determined pulmonary function to the patient, for example, to provide for alerting the patient whether the patient's determined function indicates whether the patient should continue the inhalation drug therapy program or seek immediate medical attention, and (3) monitoring changes in the determined pulmonary function.

It is another object to provide a flow transducer system that senses flow passing in one direction over a first flow range and senses flow passing in the other direction over a second flow range so that an optimized resolution scale is obtained using the same processing electronics for the different flow ranges in the different directions.

It is another object of the invention to provide for calibrating a durable flow transducer system having different flow sensing ranges in different flow directions. It is another object to calibrate such a durable flow transducer system with an array of data points spanning the two flow ranges and providing piecewise interpolation between data points.

It is another object of the present invention to provide a programmable, durable variable dose inhaler whereby the medication being administered and the time release of medication can be selected, and the inhaler can be programmed to provide for efficacious delivery of the selected medication to a given patient. It is another object to provide an improved inhaler with audible, visual or audiovisual feedback for prompting the patient to obtain a suitable breathing pattern for delivering a selected medication at an appropriate time based on the patient's detected inspiratory flow and, optionally, for measuring a selected pulmonary function.

It is another object of the invention to provide a durable, portable, battery-powered device for administering aerosolized medication having a disposable cassette containing the medication to be administered, and a durable body for receiving the cassette, the body having a calibrated flow transducer system, an actuator mechanism device for releasing a dose of medication from the cassette, an actuator release mechanism for actuating the actuator mechanism in response to the sensed flow satisfying the provided delivery threshold, and control electronics.

It is a further object of the present invention to provide a disposable cassette of medication with an electronic circuit or other code for uniquely identifying the cassette, including the type of medication contained therein. It is another object to provide such a cassette with a nonvolatile memory device and optionally a power supply.

It is another object of the invention to provide a durable, portable, battery powered device for delivering aerosolized medication including a uniquely coded disposable cassette and a durable body having a circuit for reading the cassette code to identify the cassette and/or the medication to be delivered.

It is another object to provide a disposable mouthpiece containing a nozzle for dispensing medication, and a non-disposable flow rate sensor located in the flow path to detect flow which does not interfere with generation of an aerosol for inspiration by a patient.

It is another object of the invention to provide for determining variations of the flow rate sensor output unrelated to variations in flow over time and to correct such variations. It is another object to provide drift offset correction of a flow transducer output in real time during operation.

The aforementioned U.S. patent application Ser. No. 664,785, copending and commonly assigned, provides methods and apparatus for delivery of aerosol medications for inspiration which increases the effectiveness and utility of devices for delivering aerosolized medications and which overcomes many problems of the prior known devices. That application concerns methods and apparatus based on detecting the patient's inspiratory flow and releasing a controlled amount of an aerosol medication as one or more pulses at one or more corresponding identified points in the detected inspiratory flow, to provide an efficacious delivery of a selected amount of medication.

Each pulse may be provided with a pulse width, shape, and frequency that will provide the respirable fraction of the aerosolized compound being delivered and the cumulative particle size distribution so as to enhance delivery of the aerosolized compound to desired loci in the airway. The time the valve is opened is selected to produce an aerosol mist having a cumulative particle size distribution selectively favoring small or large particles, as desired. The time open is selectable between 10 and 1000 msec. The valve may be operated asynchronously or synchronously to produce one or more pulses such that each full dosage of aerosol includes one pulse or more than one pulse of non-uniform or uniform pulse widths, shapes, and intervals between pulses.

The delivery threshold may be based on an inspiratory flow rate, more particularly, a selected rate prior to the occurrence of the peak inspiratory flow rate, e.g., for a preselected threshold a rate in the range of 20 to 30 liters per minute, an inspiratory flow volume, e.g., for a preselected threshold a volume of about 1.0 liter. More preferably, the delivery threshold is a combination of a flow rate parameter and a flow volume parameter as, e.g., a pair.

The U.S. application also refers to methods and an apparatus for delivering an aerosol from a supply of aerosol generating material for inspiration by a person in response to the detected inspiratory flow of the person. One such apparatus includes:
a valve in communication with the supply of aerosol generating material;
means for operating the valve to release an amount of aerosol generating material to form an aerosol;
means for detecting an inspiratory flow of the person;
means for controlling the valve operating means in response to the detected inspiratory flow comprising:
  first means for determining whether each detected inspiratory flow is one of a first flow or a subsequent flow, the first flow corresponding to one of the first attempt to deliver an amount of aerosol and the first attempt to deliver an amount of aerosol following delivery of an amount of aerosol, the subsequent flow corresponding to an inspiratory flow detected subsequent to a preceding detected inspiratory flow not followed by delivery of an amount of aerosol;
  means for providing a delivery threshold corresponding to a point in the detected inspiratory flow at which an amount of aerosol is to be delivered, the provided delivery threshold being a preselected delivery threshold in response to the detected inspiratory flow being determined to be a first flow, and a determined delivery threshold in response to the detected inspiratory flow being determined to be a subsequent flow, the providing means including means for calculating the determined delivery threshold based on the preceding detected inspiratory flow; and
  second means for determining whether or not the detected inspiratory flow satisfies the provided delivery threshold so that the controlling means operates the valve to deliver an amount of aerosol in response to the second determining means determining that the detected inspiratory flow satisfies the provided delivery threshold.

The calculating means and method step for providing the determined delivery threshold determine the delivery threshold based on the detection of an inspiratory flow not satisfying the provided delivery threshold, and can determine recurvisely new delivery thresholds for each successive detected inspiratory flow that fails to satisfy each provided delivery threshold. This may be obtained by measuring a selected flow parameter of the detected inspiratory flow and adjusting the selected delivery threshold in response to the measured flow parameter. The selected flow parameter may be a point corresponding to the detected maxima of flow rate, flow volume, or some combination of flow rate and flow volume, such that the adjustment is a percentage of the detected flow parameter.

A reset flow event is declared on initialization of the system and following delivery of an aerosol in response to a sensed first flow or subsequent flow satisfying a provided threshold. It also may be declared after a preset time interval. A sensed flow following a reset flow event is treated as a first flow. Thus, a reset flow event separates successive attempts to deliver a controlled amount of a medication.

The U.S. application also discloses an embodiment in which the preselected delivery threshold is initially determined based on the person's measured inspiratory flow which is sensed as a calibration breath, and not as an attempt to deliver medication. The attempt to deliver medication is made when a subsequently detected inspiratory flow is detected and compared to the determined delivery threshold. Thereafter, the delivery is made if the detected flow satisfies the predetermined delivery threshold, and the delivery threshold is recursively lowered as in the aforementioned embodiment, i.e., based on the flow parameter of the preceding failed attempt, if any subsequently detected flow fails to satisfy the threshold. A preselected delivery schedule, corresponding to the optimal delivery threshold (and optionally additional delivery points) for the administration of the selected aerosol medication also may be determined based on the measured inspiratory flow parameters.

The means for detecting the inspiratory flow for release of medication is a tube defining an inspiratory flow path having a mouth end and an open end and a flow transducer disposed in the flow path. The flow transducer may be selected from among a flow resistive device or structure which generates a pressure drop across the device (referred to as a differential pressure transducer or structure) and an associated means for converting the measured differential pressure into an inspiratory flow rate, e.g., a pneumotach, a hot wire anemometer and means for converting the measured temperature changes into an inspiratory flow rate, and similar devices for providing a flow rate signal. The inspiratory flow path may include a means for providing a laminar flow through the inspiratory flow path so that the flow transducer detects the differential pressure across a laminar air flow. The laminar flow provides a flow and a flow path having linear characteristics for converting the differential pressures to flow rate. In embodiments not having a laminar flow means or using structures, transducers and/or inspiratory flow paths not having such linear flow characteristics, such as venturi ports or a single resistive flow screen, the flow path may be encoded by an array of predetermined calibration constants. Thus, nonlinear characteristics of the differential pressures detected across the flow resistive device may be converted by use of the calibration constant array for the range of pressures detected to flow rates, directly or indirectly. Differential pressure transducers having a differential pressure sensitivity in the range of ±25.4 cm of water corresponding to a flow rate of from about 0 to about 800 liters per minute, are described.

The U.S. application also describes methods and apparatus for monitoring the patient's breath flow patterns during the course of an aerosolized medication inspiration therapy program and determining the patient's pulmonary function, e.g., forced expiratory volume in one second, forced vital capacity, and peak expiratory flow rate, based on detected breath flow. The same flow transducer used for inspiration flow sensing also is used for measuring pulmonary function. A display device is provided for displaying the patient's determined pulmonary function quantitatively and/or qualitatively. The display device may be used to indicate the patient's instantaneous condition when an instantaneous pulmonary function is measured. The display device also may be used to indicate relative changes in condition when a subsequent measure of the pulmonary function is compared to a prior measure (or to a historical average of the measures, e.g., a weighted average) of that pulmonary function. The apparatus also may be configured to acquire a second measure of pulmonary function, compare that measure to a prior measure, and display trend data to the patient, thereby to indicate whether the person's medical condition is improving, degrading, or remaining about the same. Importantly, this display will indicate to the patient when measured functions indicate that the patient should seek medical attention.

The relative changes in measured pulmonary function may be used to adjust the dosage of medication based on the determined changes in the determined function. This may occur based on a relative change determined from one administration of medication to the next, or from a baseline measured pulmonary function (or a weighted average historical record) to the next administration of medication.

The method also includes acquiring a second breath parameter subsequent to the previously measured pulmonary function and measuring a second pulmonary function, comparing the second measured pulmonary function to the first measured pulmonary function, indicating whether or not the patient's determined pulmonary function has changed from the first to the second determinations, providing a first, second, and third visual indicators, and displaying whether the second measured pulmonary function has improved on the first visual indicator, remained nominally the same on the second visual indicator, and degenerated on the third visual indicator, relative to the previously measured pulmonary function.

It should be understood that, in the context of comparing two measured pulmonary functions, the term first breath flow or first detected pulmonary function may be one of the previously acquired measurement, a baseline measurement made at the beginning of the medication therapy, and a changing weighted average of previously acquired measurements, whereby the weights may be selected to favor more recently acquired or less recently acquired measurements. Thus, the latter acquired measurement may be compared to such a first measurement for indicating short term relative changes, absolute changes from a baseline, or more long term relative changes.

The U.S. application also refers to a portable, hand held, battery operated device for use in delivering aerosolized medications to a patient and monitoring pulmonary functions, recording pertinent information such as a calendar log of sensed flow parameters, amounts of aerosol administration together with a signal corresponding to the sensed flow parameter triggering the release, and pulmonary function.

Broadly, the present invention is directed to improvements in the construction and operation of a portable, hand-held device for delivering aerosol medication.

In one respect, the invention is directed to apparatus and methods for sensing flow in two directions over two different flow rate ranges to maximize the resolution of signal analysis in the respective ranges.

One such apparatus comprises:

a tube segment having a first end and a second end for passing a gas stream in a first direction from the first end to the second end and in a second direction from the second end to the first end, the first end having a first cross-sectional area, the second end having a second cross-sectional area;

an asymmetrical orifice disposed between the first and second ends of the tube including a throat having a third cross sectional area that is less than the first cross-sectional area and less than the second cross-sectional area and having a first pneumatic impedance to flow in the first direction and a second pneumatic impedance to flow in the second direction;

a pressure tap terminating in the tube between the first end and the throat and in communication with the flow in the tube; and a transducer in communication with the pressure tap having an output signal corresponding to the pressure at the pressure tap termination, the transducer output signal having a range corresponding to a first range of flow parameters for flow passing in the first direction and to a second range of flow parameters for flow passing in the second direction.

Preferably, the asymmetrical orifice has a ramp transition extending between the first end and the throat and a step transition or an undercut between the throat and the second end.

One such method for measuring a flow parameter of a gas flow in a first direction within a first range of flow parameters and a flow parameter of the gas flow in a second direction within a second range of flow parameters, the first and second directions being opposite, comprises:

providing a tube segment having a first end with a first cross-sectional area, a second end with a second cross-sectional area, and an asymmetrical orifice between the first and second ends, the asymmetrical orifice presenting a first pneumatic impedance to the flow in the first direction and a different pneumatic impedance to the flow in the second direction;

providing the orifice with a throat and a cross-sectional area at the throat that is smaller than the first and the second cross-sectional areas;

passing the gas flow through the tube segment in one of a first direction from the first end to the second end and a second direction from the second end to the first end;

measuring the pressure of the flow in the first direction through the orifice at the first pneumatic impedance and measuring the pressure of the flow in the second direction at the different pneumatic impedance within a range of pressures at a pressure tap located between the first end and the throat;

determining the direction of flow; and converting the sensed pressure into the selected flow parameter, wherein, for sensed flow in the first direction, the range of pressures corresponds to a first range of flow parameters and, for sensed flow in the second direction, the range of pressures corresponds to a second range of flow parameters different than the first range.

The calibration table preferably comprises a plurality of data points respectively in the first and second flow parameter ranges, and converting the voltage signal further comprises interpolating between data points in the corresponding calibration table based on the sensed pressure and the direction of flow. Preferably, the difference between the first and second ranges is selected from between a ratio of 2:5 to 1:100, and more preferably the first range is on the order of from 0 to 720 liters per minute and the second range in on the order of from 0 to 200 liters per minute.

In another aspect, the present invention is directed to automatic calibration of a flow transducer over two different (inhale and exhale) flow ranges. One such method of calibrating the output of a transducer for sensing flow for use in a durable flow path having two non-linear flow characteristics in opposite directions therethrough over different ranges of flow, comprises:

(a) mounting the durable flow path in a fixture and simulating the manner in which the flow path will be used to sense flow;

(b) providing a flow controller having a controllable calibrated flow rate;

(c) selecting a first direction of flow through the tube and assigning a first plurality of data points defining a first flow rate range for the first direction, each of said first plurality of data points having a known flow rate;

(d) passing air at a first known flow rate into the tube in the first direction and monitoring the signal output by the transducer in response to the first known flow rate;

(e) repeating step (d) for each other known flow rate in the first plurality of data points;

(f) deriving a first calibration array correlating the sensed transducer output with the corresponding known flow rate for each of the first plurality of data points;

(g) selecting a second direction of flow through the tube and assigning a second plurality of data points defining a second flow rate range for the second direction, each of said second plurality of data points having a known flow rate;

(h) passing air at a second known flow rate into the tube in the second direction and monitoring the signal output by the transducer in response to the second known flow rate;

(i) repeating step (h) for each other known flow rate in the second plurality of data points;

(j) deriving a second calibration array correlating the sensed transducer output with the known flow rate for each of the second plurality of data points; and (k) providing the first and second calibration arrays for determining the sensed flow in the first and second directions respectively.

BRIEF DESCRIPTION OF THE DRAWINGS

Further features of the invention, its nature and various advantages will be more apparent from the accompanying drawings and the following detailed description of the invention, in which like reference numerals refer to like elements and parts, and in which:

FIG. 4 is an elevated perspective view of the replaceable cassette of FIG. 1;

FIG. 5 is an exploded view of the replaceable cassette of FIG. 4;

FIG. 15 is a top perspective view of the driver of FIG. 6;

FIG. 16H is a front view of the chassis of FIG. 3;

FIG. 17A is top view taken along line 17A—17A of FIG. 3 of the airway cover of FIG. 1;

FIG. 17B is a cross-sectional view taken along line 17B—17B of FIG. 17A;

FIG. 17C is an end view taken across line 17C—17C of FIG. 17A;

FIG. 18A is a cross-sectional view of an asymmetric orifice meter for use in the flow transducer of FIG. 1;

FIG. 18B is a cross-sectional and schematic view of the flow transducer surface of FIG. 1;

FIG. 18C is a rear view taken along line 18C—18C of FIG. 18B;

DETAILED DESCRIPTION OF THE INVENTION

Figure 1:
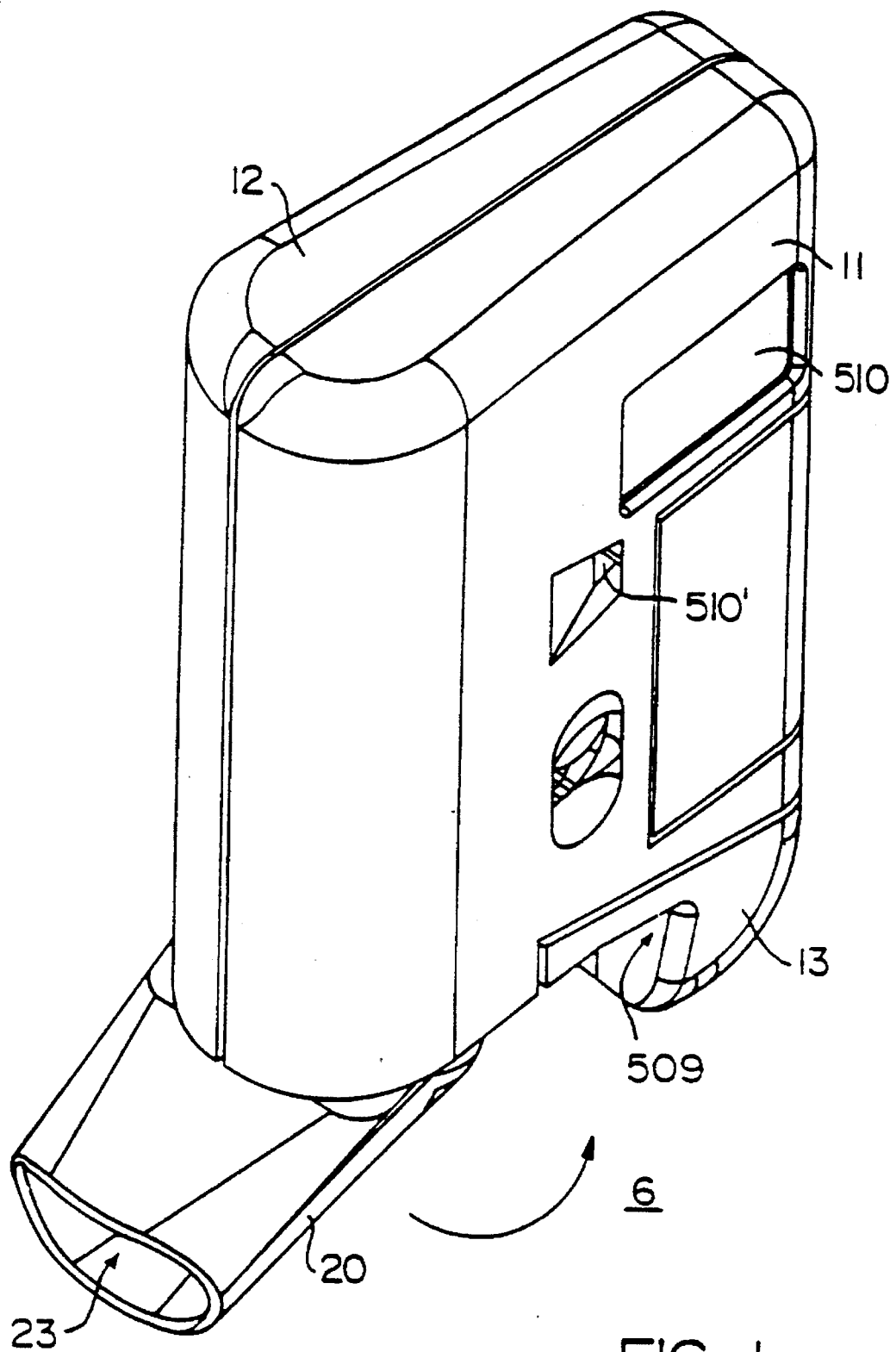
FIG. 1 is an elevated perspective view of an aerosol delivery device in accordance with a preferred embodiment of the present invention.
Figure 2:
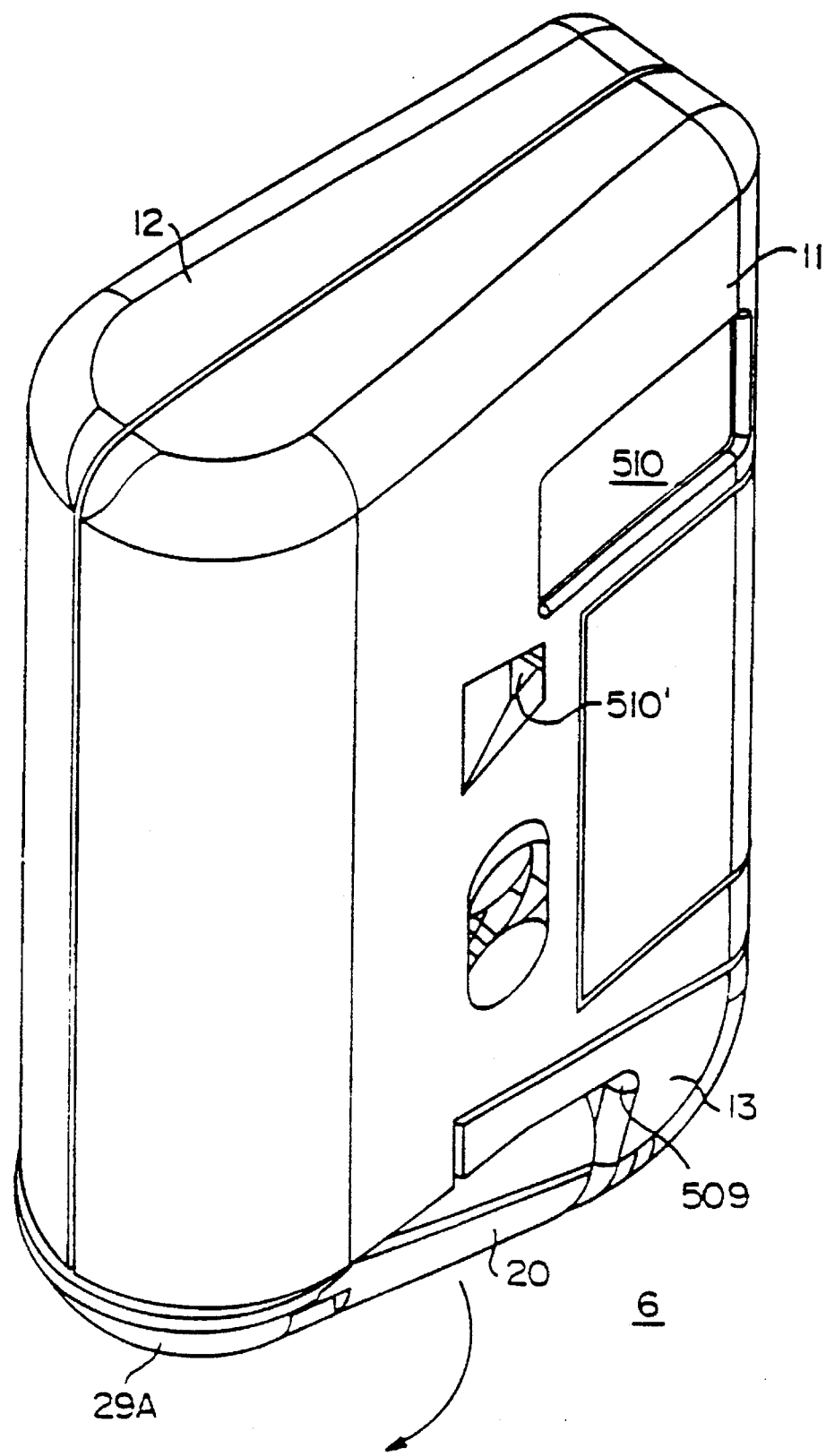
FIG. 2 is a view of the device of FIG. 1 with the mouthpiece closed.

Referring to FIGS. 1–4, an aerosol delivery device in accordance with a preferred embodiment of the present invention is shown. It includes a durable body 2 and a medication cassette 4, which interconnect to provide a hand held aerosol device 6 in accordance with the present invention. Device 6 includes an outer body 10, a mouthpiece 20, a canister containing a reservoir of medication 30 to be dispensed, a housing 40, an actuator mechanism 200, an actuator release mechanism 300, control electronics 50, a battery 60, and a flow transducer system 600.

Figure 3:
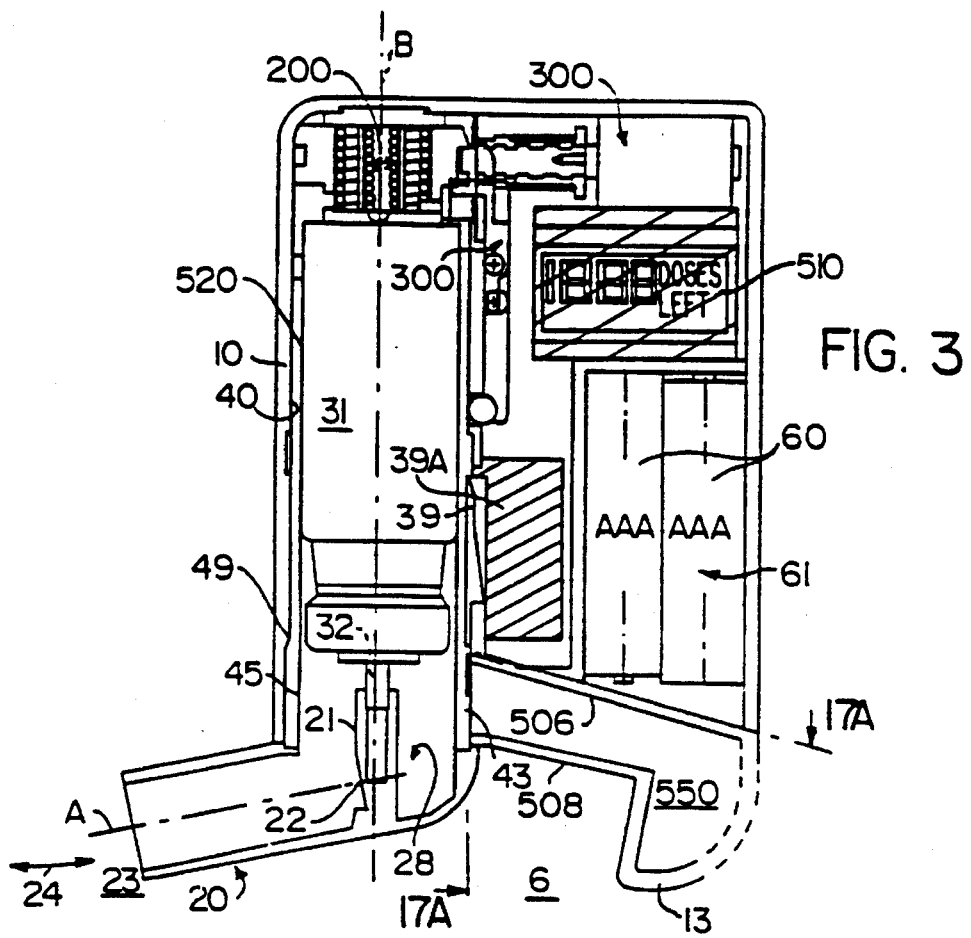
FIG. 3 is a cross-sectional view taken along line 3—3 of FIG. 1.
Figure 3A:
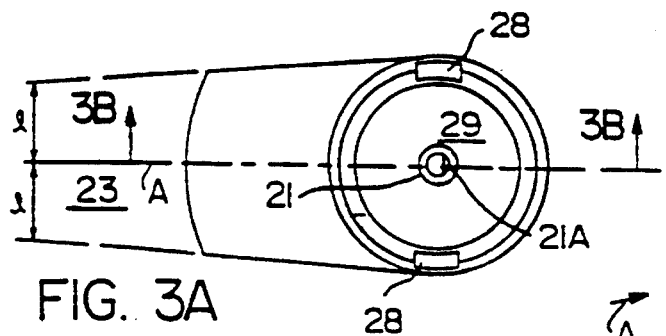
FIG. 3A is a top view of the mouthpiece of FIG. 1.
Figure 3B:
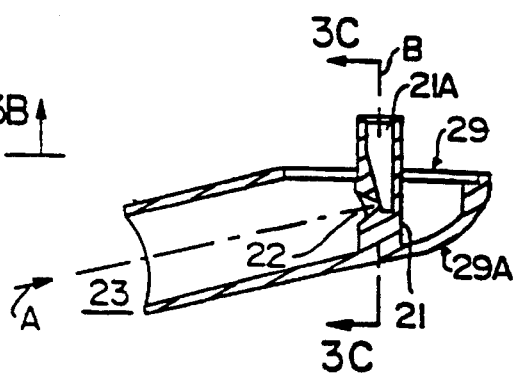
FIG. 3B is a side sectional view taken along line 3B—3B of FIG. 3A.
Figure 3C:
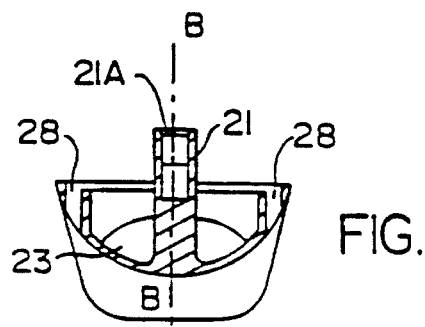
FIG. 3C is a rear sectional view taken along line 3C—3C of FIG. 3B.

Battery 60 is illustrated in FIG. 3 as two conventional AAA size 1.5 volt batteries, which are inserted in suitable receptacles in durable body 2, having an access cover panel 61. Alternate battery sources could be used, including rechargeable batteries. Battery 60 also may be replaced or supplemented by an AC/DC converter for operating device 6 off conventional line current.

Referring to FIGS. 3–5, canister 30 includes a body 31 containing a reservoir of medication to be released, a valve stem 32 for releasing an amount of the medication, and a bottom 34. Canister 30 is preferably constructed so that an amount of the stored medication is released when valve stem 32 is sufficiently pressed relative to body 31 (also referred to as "held down" or "depressed").

In the preferred embodiment, canister 30 and valve stem 32 are part of a standard metered dose canister such as can be used with conventional manually operated metered dose inhaler devices. In an alternate embodiment, canister 30 and valve stem 32 may be constructed as a simple valve and reservoir body 31 which operates to release an aerosol for as long as valve stem 32 is sufficiently depressed relative to body 31. Thus, the dose released by a straight valved canister can vary with the time valve stem 32 is maintained depressed. Both canister constructions include internal return springs (not shown) that return valve stem 32 to the outer position which seals the reservoir closed to the atmosphere, when the actuating force is removed.

The reservoir in canister 30 may contain any selected medication (or other material to be delivered) in liquid, gas, or dry powder form. Where appropriate, a suitable propellant or carrier or an agitator for forming an aerosol of the liquid, gas or powder for delivery to the patient also is provided.

Canister 30 is combined with mouthpiece 20 and housing 40 to form cassette 4. Cassette 4 is used to provide medication to durable body 2 for automatic release in accordance with the present invention. Cassette 4 also is constructed so that it can be used as a conventional manually actuated metered dose inhaler device, apart from the durable body 2. This is to allow the patient to obtain manual delivery of medication in the event that durable body 2, or some component thereof, fails, e.g., battery 60 is discharged. Cassette 4 is a replaceable component. It can be inserted and withdrawn from durable body 2 by the user. Thus, cassette 4 can be made disposable and/or recyclable.

Figure 16A:
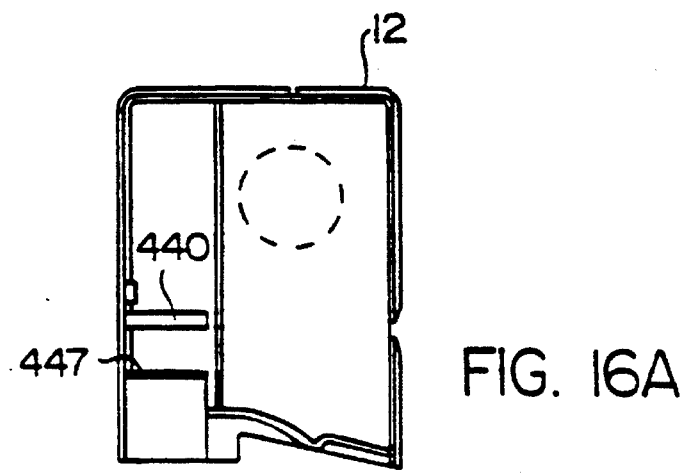
FIG. 16A, 16B and 16C are respectively side, top and bottom views of one housing of the durable body of FIG. 1.
Figures 16B, 16C:
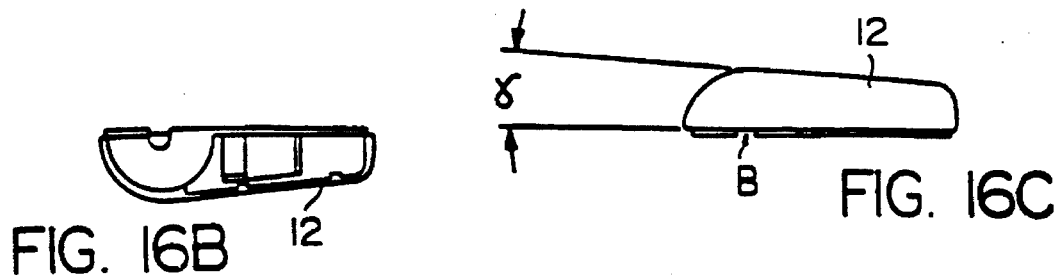

Housing 40 is constructed with an interior shape that corresponds to the shape of canister body 31, e.g., a cylindrical structure. Housing 40 also is constructed with an outer shape that fits into a complimentary shaped receptacle 520 in durable body 2. Housing 40 has a bottom end 45 having an outer dimension that is larger than the outer dimension of the top portion. The dimension of bottom portion 45 provides a bearing seat 47 which contacts a ledge 447 built into a receptacle 520 of durable body 2 for proper placement of cassette 4 (see FIGS. 16E, 16G). A pair of locking tabs 42 extend downwardly from bottom end 45. Tabs 42 are configured to interfit lockingly with a pair of corresponding apertures 28 in mouthpiece 20 to secure canister 30 inside and between mouthpiece 20 and housing 40.

Housing 40 has at its top end 46 an in-turned annular flange 48 which is dimensioned to hold canister 30 in place inside cassette 4 with valve stem 32 seated in valve stem receptacle 21, but not depressed relative to body 31. This provides for securing the medication inside cassette 4 so that the patient cannot remove easily the canister 30, or more preferably cannot be non-destructably removed from the cassette. Annular flange 48 also is dimensioned to permit a person to depress canister 30 manually, pressing body 31 relative to valve stem 32, to release a dose of medication. Most canisters 30 containing a blend of medication and propellent under pressure have a concave bottom 34. Therefore, it is advantageous to provide a disk 35 between flange 48 and canister bottom 34. Disk 35 thus makes it easier to operate manually canister 30. Disk 35 may be flat or convex and may be made of a rigid plastic or metal.

In an alternate embodiment, cassette 4 is made to be reusable with different canisters 30, and flange 48 is omitted. In such case, a frictional engagement of valve stem 32 and valve stem receptacle 21 will hold canister 30 inside housing 40. In yet another embodiment, cassette 4 may be sealed at end 46 so that it cannot be manually actuated. This is useful where the medication to be delivered is a narcotic and is to be dispensed only by the durable body under programmed control.

The top portion 46 of housing 40 also includes two notches (or apertures) 49. These are used by a driver element of actuating mechanism 200 in connection with the automatic release of medication and is described below.

Housing 40 also contains a multi-bit code which is representative of its contents. In one embodiment, as illustrated in FIGS. 4 and 7–9, the code is in the form of a series of protrusions 41 (or hubs) on its periphery at a selected location. In order to insert fully and correctly cassette 4 into body 2 to form an operable device 6, protrusions 41 must mate with a corresponding slotted disc or keyplate 440, which has previously been secured to a chassis 400 inside durable body 2 (see FIG. 6). The keyed protrusions 41 and keyplate 440 thus may be used to provide for medication identification and a level of protection against inserting the wrong or an unauthorized medication into body 2.

In one embodiment, there are a maximum of six protrusions 41 spaced to provide physically a six bit codeword, based on the presence or absence of a protrusion 41 at each location. Each durable body 2 may thus be provided with a keyplate 440 that is constructed to receive only cassettes 4 having one selected codeword matching keyplate 440. This construction provides for a dedicated durable body 2 which can only be used to deliver medication from a cassette having the one code, unless the keyplate 440 is changed.

In an alternative embodiment, multiple bit words represented by protrusions 41, may be used to identify the pertinent delivery characteristics for a selected medication. Such information may include the concentration and dosage delivery information, how many dosages are in the canister 30 initially, the dosage frequency, time between successive dosages, when during the inspiration the dosage is to be released, the duration of the release of dosages or some combination of the foregoing. This may be achieved by assigning to each codeword a delivery protocol for the particular parameters to be used by control electronics to delivery medication. Thus, durable body 2 is adapted to read the multi-bit code provided by protrusions, e.g., by a series of microswitches which are pressed closed by protrusions 41, look up in a library of stored delivery protocols the codeword read, and select from the library the corresponding delivery protocol which is loaded into the control electronics 50 for administering the medication. In this alternate embodiment, the medication identification also may be a part of the codeword. It is noted that more or less than six bits and corresponding protrusions 41 could be used. Similarly, the codeword read could be an identification code for the selected medication, which could be determined from a library along with the correct delivery parameters for that medication.

In yet another alternative embodiment, instead of or in addition to physical protrusions 41, an active or passive electronic circuit element 41B (see FIGS. 4 and 9) is provided which provides code information to a corresponding decoder circuit in durable body 2 (not shown). Such an electronic circuit could be an impedance value having a corresponding delivery protocol and/or medication identification meaning, a digital codeword or, in an even more sophisticated version, a memory device containing electronically readable data, e.g., a read only memory (ROM) device, programmable read only memory device (PROM), nonvolatile random access memory (RAM) or the like. Such a memory device may contain one or more codewords that identifies the medication, the number of dosages of medication in canister 30, and optionally the delivery protocol (complete or pertinent parts) for that medication. In such case, durable body 2 will have electrical contacts (not shown) for connecting to the electric circuit 41B and obtaining the code and/or data contained therein digitally, serially, in parallel, or as an analog signal value.

Further, the electronically readable code and/or data could identify each canister (or cassette) uniquely. This permits durable body 2 to record a log of use for each individual canister 30 inserted and maintain a running count of the number of dosages remaining in a given canister 30 or the number of dosages delivered from that canister 30. This unique identification permits a patient to deliver more than one medication using different medication cassettes 4 and the same durable body 2. In this embodiment, durable body 2 contains corresponding sensing contacts (not shown) that mate with cassette 4, e.g., during insertion of cassette 4 into body 2, or whenever cassette 4 is placed in the open position, to read the information represented by protrusions 41 and/or any electronic circuit 41B. Optionally, the electrically readable data could be downloaded into memory in control electronics 50, e.g., during insertion, and off loaded back to the cassette, e.g., during withdrawal. This would obviate the need to always be connected to the cassette electrical circuit 41B. Different uniquely identified cassettes 4 may be used in the same durable body 2, whereby control electronics 50 can maintain separate counts of remaining dosages and/or delivered dosages for each cassette 4 by using the unique identification code as an address.

In yet another alternative, cassette 4 provided with memory 41B containing programming information for use by durable body 2 may be reprogrammed by durable body 2 so as to maintain in memory 41B an accurate count of the number of doses remaining and/or already delivered, and other sensed parameters that are logged. This will permit using the same cassette 4 in different durable bodies 2 without losing the count or other logged information.

Referring again to FIG. 6, the larger protrusion 41A is used for aligning cassette 4 for insertion into body 2 in the first instance and for retaining cassette 4 inside chassis 400 of durable body 2 except when protrusion 41A is aligned for insertion and removal. A vertical recess 406 is provided in chassis 400 (or in receptacle 520) to guide cassette insertion and extraction so that protrusions 41 align with keyplate 440. The alignment also is used so that actuator mechanism 200 will seat easily in notches 49. In the preferred embodiment, referring to FIG. 3, the insertion/extraction position is when mouthpiece 20 is in the open position for administering an amount of medication (as illustrated in FIG. 1) and a latch 39 is used to fit underneath protrusion 41A to hold cassette 4 in receptacle 520, once it is fully inserted. A spring 39A is used to bias latch 39 under protrusion 41A as soon as cassette 4 is seated. A button or slide (not shown) is used to retract pin 39 for extraction of cassette 4 from body 2.

An annular recess 405 is provided in chassis 400 (and/or receptacle 520) for receiving protrusion 41A whenever cassette 4 is fully inserted in body 2 and in other than the insertion/extraction position (see FIG. 16H). Annular recess 405 is used to prevent cassette 4 from falling out of durable body 2 inadvertently.

Bottom portion 45 of housing 40 includes an aperture 43 which cooperates with mouthpiece 20 to form a flow path 24 through mouthpiece 20 and the bottom portion 45 of housing 40. When mouthpiece 20 is in the open position, aperture 43 cooperates with airway cover 13 to provide flow communication through device 6 as discussed below. Housing 40 is preferably made of a polypropylene material, which is preferably clear. This permits the user to read the product labeling provided by the manufacturer of the medication canister through the housing walls. It also avoids the necessity to provide drug labeling on housing 40. Housing 40 is preferably recyclable.

Referring to FIG. 4, housing 40 also includes a location mark 44, preferably in the form of a surface indentation or protrusion, more preferably an indentation located a selected distance from or on the aforementioned bearing seat 47 on housing 40. Location mark 44 cooperates with a suitable contact switch 460, e.g., a Omron model D2MQ-1 available from Digi-key, Thief River Falls, Minn., suitably positioned in durable body 2. This contact switch provides a signal to control electronics 50 indicating when cassette 4 is in the open position for delivering medication.

Referring to FIGS. 3, 3A, 3B, and 3C, mouthpiece 20 is a tubular body that has a mouth end opening 23, a top end opening 29, a valve stop 21 which incorporates a flow path 21A and a nozzle 22, a pair of apertures 28, and provides a flow path 24 generally along an axis labeled A passing through the center of mouth end 23 and nozzle 22. Nozzle 22 and its flow path 21A are conventional in design and directed to release an aerosol cloud along axis A. A preferred embodiment of nozzle 22 and flow path 26 includes 0.018 inch (0.46 mm) diameter orifice for nozzle 22 and a 0.94 inch (23.88 mm) diameter for flow path 26.

Mouthpiece 20 is illustrated as having a symmetrically squashed oval tube, with rounded sides and relatively flat top and bottom faces. The interior dimensions should be selected not to interfere adversely with the dispersion pattern of an aerosol released at nozzle 22 during an inhalation. The outer dimensions are selected to be comfortable for a patient to engage with their lips with a reasonable air-tight seal. Mouthpiece 20 may be made of a polypropylene material.

Top end 29 of mouthpiece 20 opens to mate with bottom portion 45 of housing 40. The squashed oval section of mouthpiece 20 is contoured to blend into a rounded and curved inside or bowl-like back section generally illustrated as region 29A. Region 29A allows the flow to pass between aperture 43 of housing 40 and mouth end 23 sufficiently smoothly to entrain an aerosol generated by nozzle 22 during an inhalation. It also permits flow in the other direction for measuring exhalation. Preferably, the mouthpiece flow axis A intersects with the back wall of region 29A near the interface of mouthpiece 23 and housing 40. Aperture 43 is a substantially rectangular opening (when the curved wall is flattened) that is about as wide as the diameter of top end 29 and has a height that in the curved shape has a chord about 75% of the height of mouth end 23. Other dimensional relationships could be used.

As noted, apertures 28 provide for receiving housing tabs 42 and securely locking together housing 40 and mouthpiece 20. This is so that the patient cannot remove canister 30 from housing 40 without considerable effort. Locking tabs 42 and apertures 28 also cooperate to transfer force from a compression spring 210 to protrusion 41A and locking pin 39, and to rotate cassette 4 in body 2, after insertion, by turning mouthpiece 20 about the axis B formed by valve stop 21 flow path 21A, and canister 30. The locking tab aperture construction should be understood also to include having one or both of the locking tabs projecting from the mouthpiece and fitting into a corresponding aperture in the housing.

In an alternative embodiment (not shown), in place of locking tabs 42 and apertures 28, mouthpiece 20 and housing 40 could interfit in a manner that permits separation for replacing canister 30 inside and reusing housing 40 and/or mouthpiece 20 for a different canister 30 and for cleaning mouthpiece 20 and nozzle 22. This may be obtained, e.g., by a threaded interconnection or a bayonet-type connection between housing bottom 45 and mouthpiece top and opening 29, provided that cassette 4 can be rotated about axis B by the mouthpiece 20 without mouthpiece 20 separating from housing 40. Care must be taken to be sure that the force from compression spring 210 will not cause mouthpiece 20 to separate from housing 40 or change the axial distance between mouthpiece 20 and protrusion 41A. Such a design is useful for adapting standard metered dose canisters for use in the present invention and permitting the patient to obtain refills of the same medication from sources, e.g., other than the source that supplied the cassette.

Referring now to FIGS. 3 and 6–15, actuator mechanism 200 and actuator release mechanism 300 provide for electromechanically firing canister 30, under control of control electronics 50, in response to the sensed inspiratory flow satisfying a provided flow delivery threshold. The predetermined flow delivery threshold may be a selected flow rate, a selected flow volume, or some combination of the two. In the preferred embodiment, the flow delivery threshold is a combination of the sensed flow rate being within a range defined by a selected minimum flow rate threshold and a maximum flow rate threshold, and the flow volume being within a range defined by a selected minimum volume threshold and a maximum volume threshold.

The delivery threshold is satisfied in the following manner. First, the sensed flow rate is checked. If the flow rate is in the correct range between the upper and lower limits, the flow volume is checked. If the flow volume also is in the correct range between the upper and lower volume limits, then the delivery threshold is satisfied and a delivery will occur. Otherwise delivery is inhibited.

If delivery is inhibited for the entire inhalation, then the flow volume and flow rate threshold parameters may be lowered recursively. In this regard, during the inspiratory flow, the flow transducer system monitors and stores the peak flow rate and the total inhaled volume. At the end of the inhalation, which is sensed by passing through a zero flow state, control electronics check to see if a delivery event occurred. If it did, then the shot count of doses remaining and/or delivered is updated and the system waits for the next inhalation (and delivery attempt). Control electronics also may include a timer to prevent too frequent delivery of medication (overmedication).

If a delivery was not made, then the delivery threshold is checked. More specifically, the peak flow rate and inhaled volume values of the flow that failed to cause a delivery are reduced by a selected percentage, e.g., 25%. The reduced values are compared to respective preselected (programmable) default values for the minimum flow rate and flow volume thresholds. If the percentage of the sensed peak flow rate for the failed breath is less than the default minimum flow rate threshold, then it is used as the minimum flow rate threshold for the subsequent detected breath. Otherwise the default value is used. Similarly, if the percentage of the sensed total volume for the failed breath is less than the default minimum flow volume value, it is used as the minimum flow volume value for the subsequent breath. Otherwise the default value is used. If the subsequent breath also fails, then its sensed peak flow rate and inhaled volume are similarly processed in this recursive manner, to select new delivery threshold suited to the patient's condition at the time of delivery.

In one useful embodiment, the default values, each of which is programmable, are: upper flow rate 80 l/m, lower flow rate 40 l/m, upper flow volume 1.25 l, and lower flow volume 1.0 l. Although in the preferred embodiment the upper limits are not recursively changed, in an alternate embodiment they could be changed, e.g., as a selected multiple of either the lower thresholds or the sensed peak values. Other flow delivery threshold parameters also may be used.

The actuator mechanism 200 includes a compression spring 210, a helical torsion spring 220, a rotary (helical) cam 230, and a driver 240. Each of these elements is oriented in axial alignment with the longitudinal axis B of canister 30. The actuator release mechanism 300 includes a trigger mechanism and a motor 321 for driving the trigger mechanism, which are located off of axis B.

Figure 13A:
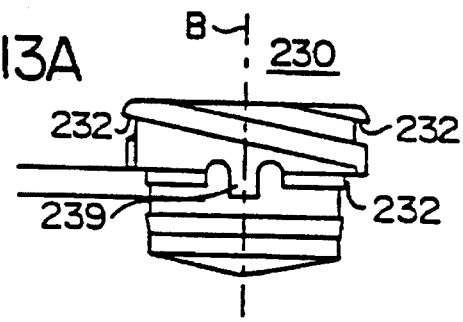
FIG. 13A and 13B are respectively a side view of and an unwrapped view of the rotary cam of FIG. 6.

Rotary cam 230, which is illustrated also in FIGS. 13A, has a first cam surface 232 which cooperates with a pair of cam followers 430. Cam followers 430 are attached to chassis 400 in durable body 2 on opposite sides of cam 230 in an appropriate location. Rotary cam 230 will thus rotate in one direction with cam surface 232 sliding against cam followers 430 so that rotary cam 230 moves upwardly along axis B shown in FIG. 6 as it rotates. Rotary cam 230 has no effective lower cam surface. This allows cam 230 to move downwardly along axis B without rotating. Vertical motion is imparted by release of compression spring 210. Rotary motion is imparted by release of torsion spring 220. The distance that cam 230 translates up and down corresponds to the distance valve stem 32 must be depressed relative to canister body 31 to release a metered dose of aerosol. For standard metered dose inhaler canisters 30, the distance the valve stem must be depressed is on the order of 0.1 inch (2.5 mm). Cam 230 may be made of any suitable material, such as DELRIN AF.

Figure 13B:
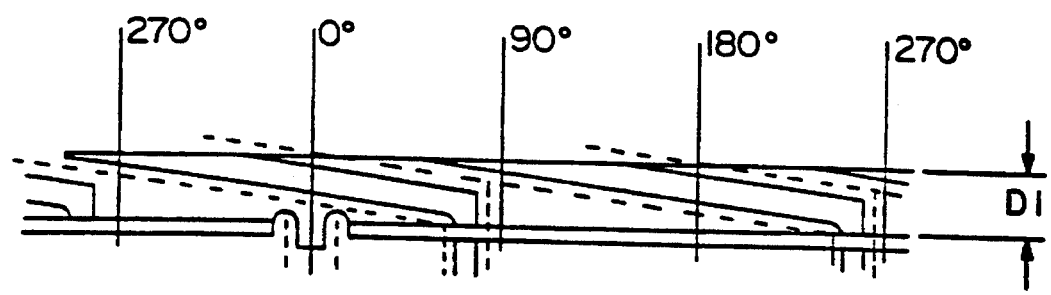

Referring to FIG. 13B, rotary cam 230 is illustrated in an unwrapped view illustrating the 0.333 inch (8.46 mm) pitch, a height of 0.227 inches (5.77 mm), a distance D1 of 0.1 inch (2.5 mm) plus the thickness of cam followers 430, and a helical face cam.

Figure 6:
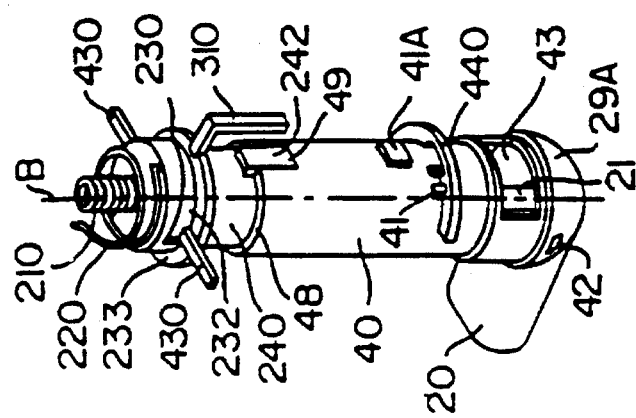

Rotary cam 230 is secured at its top to compression spring 210 and to torsion spring 220, as shown in FIG. 6. The other ends of springs 210 and 220 are fixed, e.g., to chassis 400 or body 2. Rotary cam 230 is secured at its bottom to release ring 233, by a keyed interconnection including key protrusion 239 (shown in face view of FIG. 13A) of cam 230 and slot 235 of release ring 233. Cam 230 does not rotate relative to release ring 233.

Figure 14A:
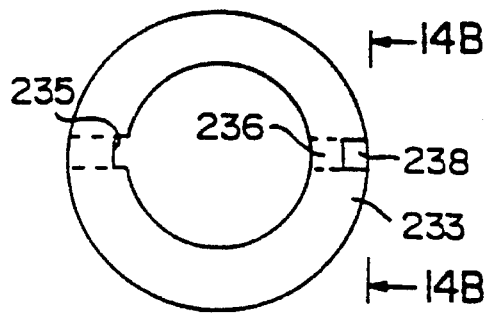
FIG. 14A is a top plan view of the release ring of FIG. 6.
Figure 14B:
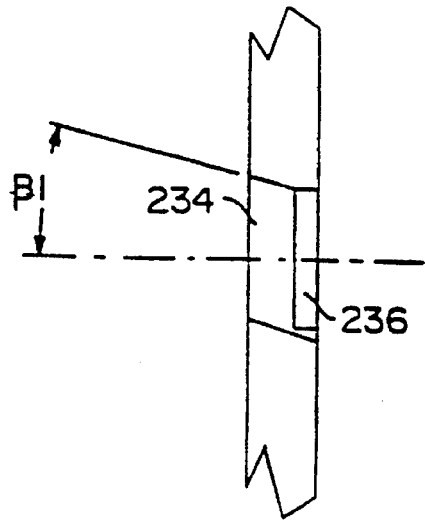
FIG. 14B is a side view taken along line 14B—14B of FIG. 14A.

Referring now also to FIGS. 14A and 14B, release ring 233 is an annular ring, having a radial groove (or recess) 236, a radial slot 234, and a keyway 235 for securing release ring 233 to cam 230. Release ring 233 also may be surface treated to improve hardness, e.g., chrome plating. It is preferably a hardened tool steel ring (65–70 Rockwell C).

Referring now also to FIGS. 6–10, 11, 11A, and release ring 233 and its radial groove 236 and radial slot 234 cooperate with the trigger mechanism and motor 321 as follows. The trigger mechanism 310 includes a trigger pin 312 with a generally rectangular cross sectional base 311 and a multifaceted tip 313. As shown in FIG. 6, trigger pin 312 has a first position where the top surface 343 of its tip 312 rests underneath release ring 233 in groove 236, with compression spring 210 in compression and torsion spring 220 in torsion. Compression spring 210 biases release ring 233 downwardly with groove 236 receiving trigger pin tip 313 securely seated inside. Torsion spring 220 biases release ring 233 to rotate, but trigger tip 313 being inside groove 236 and/or slot 234 prevents such rotation.

In accordance with the present invention, top surface 343 of trigger tip 313, which is in contact with groove 236 on the bottom of release ring 233, is cut at an angle α1 to the top surface 342 of base 311. Surface 342 is essentially parallel to the plane of release ring 233. Consequently, the downward pressure exerted by compression spring 210 acts on surface 343 to urge trigger pin 312 out from underneath release ring 233. However, trigger pin 312 is maintained in the first position, under release ring 233, by motor 321 (not shown in FIG. 6), in a manner that is described below.

Figure 7:
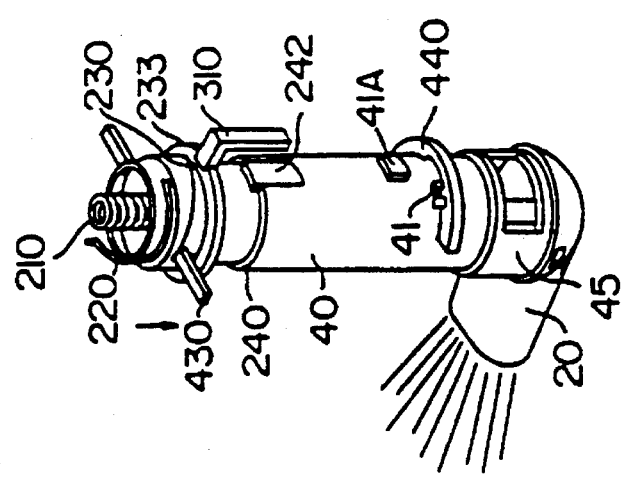

Referring to FIG. 7, the trigger mechanism has a second position where trigger pin 312 is moved out from groove 236 and under release ring 233 and is located in slot 234. Slot 234 and groove 236 are in radial alignment, with slot 234 being located in the outer perimeter of release ring 233. This is illustrated in FIG. 14B. This movement allows slot 234 to move downwardly, straddling trigger pin 312, and as a result depresses canister 30. Torsion spring 220, however, biases release ring 233 so that slot 234 presses against a side wall 341 of trigger tip 313. Consequently, torsion spring 200 remains in torsion.

Side wall 341 also is provided with an angle α3 relative to base wall 311A (see FIG. 12B) which responds to the rotational pressure exerted by the opposing inner wall of slot 234 to urge trigger tip 313 out of slot 324. The result of this ejection, when it occurs, is that release ring 233 (and rotary cam 230) will rotate as torsion spring 220 releases. However, motor 321 retains trigger pin 312 in its second position for a selected time period, so that cam 230 does not rotate (not shown in FIG. 7), as will be described below. Side wall 341 also is cut at an angle α2 relative to the wall of base 311 opposite to wall 311A to correspond to release ring 233 to minimize or reduce energy lost from compression spring 210 due to friction, thereby to maximize the energy transfer from spring 210 to canister 30. The front end wall 311B may be cut at an angle suitable to provide clearance as tip 313 pivots, as described below.

Figure 12:
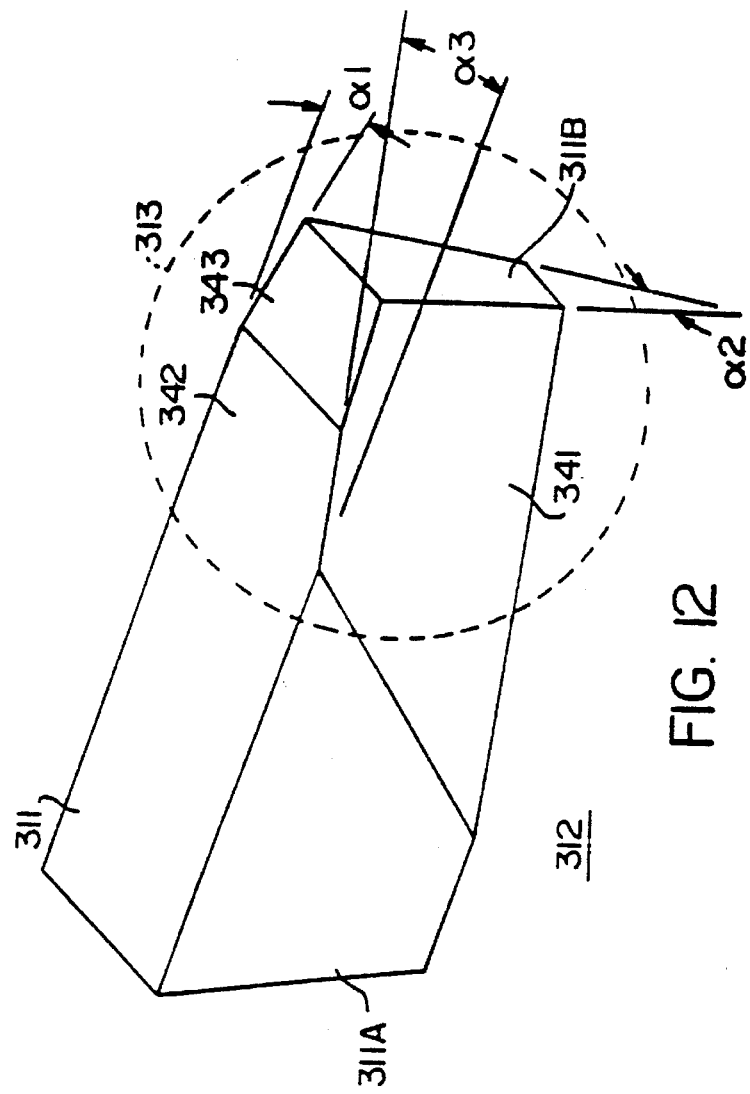
FIG. 12 is an elevated perspective side view of the trigger pin tip of FIG. 11.
Figure 11A:
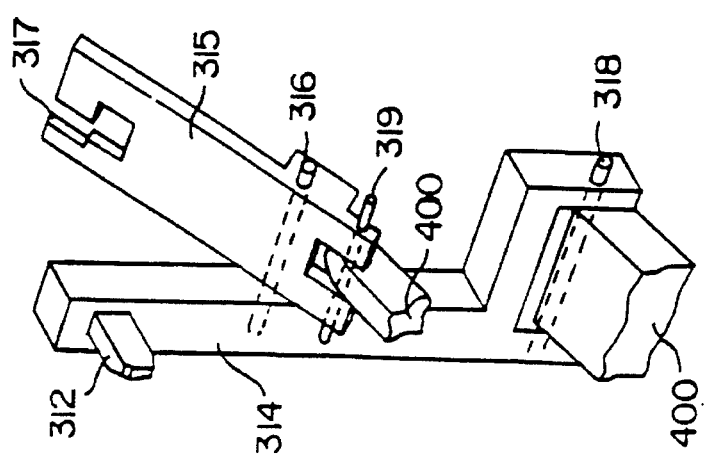
FIG. 11A is a front elevated perspective view of the compound lever trigger mechanism of FIG. 11.

Slot 234 is configured with its walls cut at an angle β1 relative to axis B as shown in FIG. 14B. Referring to FIG. 12 trigger pin tip 313 top surface 343 is formed at an angle α1 relative to a plane horizontal to axis B, and trigger tip side surface 341 is provided with an angle of α3, relative to a plane parallel to axis B. The angles α1, α2, α3 and β1 are selected so that predetermined force magnitudes, which, if not counteracted by motor 321 holding trigger pin 312 in position, would cause trigger pin 312 to be forced out from under ring 233 to release compression spring 210 to deliver medication, and then out from slot 234 after the release of medication to release torsion spring 220 to recock compression spring 210. Although the angles are a matter of design choice, one suitable angle for each of α1, β2, β3 and β1 has been found to be about 15 degrees.

Referring to FIGS. 3, 6–11, and 15, positioned between release ring 233 and cassette 4 is driver 240. Driver 240 has a base 241 having a top surface including a stepped drive dog 245, and a lower surface that includes two drive lugs 242 and two bottom surfaces 248, as illustrated in FIG. 15. Drive lugs 242 are respectively seated in notches 49 of cassette 4 (housing 40) and bottom surfaces 248 are in contact with base 34 of canister 30 (or disk 35, if one is used). The top of base 241 has a top planar surface 243 over a first portion and a second planar surface 244 over a second portion that is in a plane below top planar surface 243. There are two step drive dogs 245 corresponding to the difference in height between surfaces 243 and 244 as illustrated in FIG. 15. One of the two steps 245 serves as a drive dog to rotate cam 230 acting on cam protrusion/step 239 whenever cassette 4 is rotated to the closed position. The other step 245 serves as a stop to prevent overrotating cassette 4 past the open position. The two steps thus limit cassette 4 to a rotation of about 180 degrees from open to closed positions. The position for insertion and withdrawal is at the full open position (180 degree position) relative to the closed position. Preferably, there are two drive lugs 242 and corresponding notches 49, although more than two of each could be used.

Driver 240 is used for cocking rotary cam 230. This occurs by rotating cassette 4 about axis B to rotate driver 240. This causes one step drive dog 245 to engage and rotate cam 230. This in turn causes cam 230 and release ring 233 to rotate and place torsion spring 220 in torsion. Release ring 233 and cam 230 are then locked in place with torsion spring 220 in torsion, when they are rotated so that the top surface 343 of trigger pin 313 engages groove 236. (See FIGS. 8–10.)

Driver 240 also is used for pressing canister body 31 downwardly, relative to valve stem 32 and cassette housing 40, to release an amount of aerosol. In this regard, the release of compression spring 210 moves rotary cam 230 and driver 240 axially downward (without rotation) along axis B. See FIG. 7, where drive lugs 242 are illustrated as fully seated in housing slots 49.

Referring now to FIGS. 3, 11, and 11A, actuator release mechanism 300 is shown comprising motor 321 and the trigger mechanism. In the preferred embodiment, motor 321 includes a lead screw 322 that rotates only in a single direction of rotation. Preferably, lead screw 322 has multistart threads, e.g., three or five starts. The trigger mechanism has a ratchet action comprising a ratchet member 323 whose movement is controlled by lead screw 322, a return spring 326, a main lever 314 and a secondary lever 315. Return spring 326 is used to return the ratchet member 323 to a starting position in the absence of an external force pressing ratchet member 323 against return spring 326. Ratchet member 323 is configured so as to catch on lead screw 322 so that an external force directed against return spring 326 causes ratchet member 323 to sit against a thread of lead screw 322. As a result, as long as the external force is applied, the position of ratchet element 323 can be controlled by rotating lead screw 322.

In one embodiment, the ratchet member 323 is a bent piece of spring steel about 0.002 inch (0.05 mm) thick having an upturned edge 324 that is secured to a pusher plate 328 by, e.g., plastic rivets 327 and 329. Rivet 329 may have an aperture 330 for passing along lead screw 322. A guide bar 325 is provided extending between a motor mount 450 and a portion of chassis 400 and parallel to lead screw 322, over which return spring 326 is passed. Guide bar 325 provides stability, minimizes binding, and prevents plate 328 from rotating. In this regard, plate 328 also has a bushing 328A having an aperture 331 which receives guide rod 325 and thus travels along lead screw 322 and guide 325, with return spring 326 between plate 328 and motor 321. Preferably, motor 321 is secured to a motor mount 450 so that spring 326 is between plate 328 and motor mount 450.

Trigger pin 312 is preferably mounted in a compound lever having a main lever 314, with trigger pin 312 protruding from one side of main lever 314, a secondary lever 315 that is pivotally connected to main lever 314 by rod 316, and a cut-out portion 317 in secondary lever 315. Main lever 314 is secured to chassis 400 so that it pivots about an axis 318 at its bottom end. Secondary lever 315 also is connected to chassis 400 about reaction pivot 319. Motor 321 may be, for example, part No. DNI2K51N1B, available from Canon, Inc. Importantly, motor 321 consumes very little current, on the order of 130 ma when the motor is running, which occurs during a 2.5 second operation, of which the motor is off for a programmable time period, e.g., one second, which is typical for releasing a dose of medication and recocking actuator mechanism 200. This amount is surprisingly less than the energy consumed by a solenoid that is used to depress canister 30.

Apertures 330 and 331 are preferably made in a low friction material, e.g., teflon, or an acetal resin such as DELRIN. Aperture 331 is configured for passing therethrough guide rod 325, such that return spring 326 is fixed between plate 328 and motor mount 450.

Motor 321 and lead screw 322 are mounted in alignment with secondary lever 315 so that lead screw 322 passes through cut-out portion 317 of lever 315. Return spring 326 biases spring metal 323 outwardly, i.e., away from motor 321, and presses plate 328 against secondary lever 315. Lever 315 is in turn biased against plate 328 by the forces exerted on trigger pin 312 by springs 210 and 220. The latter forces, when they exist, are greater than the force of return spring 326. As a result, trigger pin 312, through levers 314 and 315, presses plate 328 toward motor 321 so that upturned end 324 is pressed against and captured in a thread of lead screw 322. Thus, as motor 321 is rotated, the threads of lead screw 322 will allow upturned end 324 of spring metal piece 324 to move toward motor 321, under the pressing forces exerted by levers 314 and 315. This in turn allows trigger pin 312 to be controllably forced out from under release ring 233.

When trigger pin 312 is forced out from under release ring 233, out of groove 236 and slot 234, torsion spring 220 will release and cam 230 will rotate. As a result, cam 230 will ride up on cam followers 430 to its uppermost position. As a result of this, the forces pressing on trigger pin 312, which had been biasing upturned end 234 against release spring 236 and the threads of lead screw 322, are removed. Accordingly, return spring 326 releases and pushes plate 328 outwardly, pressing on levers 314 and 315 and trigger pin 312. This causes trigger pin 312 to be rotated into position underneath release ring 233. In this regard, it is noted that the position of cam followers 430 on cam surface 232 raises cam 230 high enough so that return spring 326 can urge trigger pin 312 in place underneath release ring 233. Lead screw 322 preferably has 12 turns per inch and 3 start threads.

To reduce the motor power requirement for the battery operated device, and hence extend the useful life, the helix angle of lead screw 322 is configured to approach, but not exceed, the friction angle between edge 324 and screw 322. This ordinarily requires a relatively large pitch, e.g., 12 turns per inch on a 0.138 inch (3.5 mm) outer diameter lead screw 322. In as much as there is no control of the rotational position of lead screw 322 when it stops, the return of edge 324 would be imprecise. It was discovered that, to increase the accuracy of the latching position where edge 324 engages a thread of screw 322, a multistart thread, specifically a three start thread is employed. Thus, where a single start had a distance of 0.088 inch between adjacent threads, a three start thread has a distance of 0.027 inch between adjacent threads. This is because the three start thread is the superposition of three one start threads each offset equally, along the screw length. This provides for improved positioning resolution without either monitoring the rotational position of screw 322, rotating screw 322, or using additional position sensing contact switches. Use of a five start thread provides improved position control.

Guide 325 and lead screw 322 provide for maintaining plate 328 and spring metal 323 properly oriented so that upturned edge 324 will again catch in one of the threads of lead screw 322 on the next advance event. In this manner, motor 321 operates only in one direction of rotation and primarily operates only as a brake to restrain plate 328 and secondary lever 315 and trigger pin 313 from withdrawing. By maintaining trigger pin 312 in place when motor 321 is stopped and not consuming electricity, motor 321 efficiently controls movement of trigger pin 312 to release a dose of aerosol medication. In contrast to prior art devices, the electrically operated motor does not provide the actuation force driving the motion of canister 30 to release the aerosol.

Upturned edge 324 is preferably bent with a curved edge, rather than a straight bend, so that it bows and is easily captured by the vertical wall of the threads of lead screw 322. Thus, upturned end 324 will be urged into a thread of lead screw 322 by lever 315, and will be passed so that it rides up and over the angled flights of the thread in succession by return spring 326 (until trigger pin 312 is placed under release ring 233 and forced back by spring 210).

Having described the apparatus components, the method of operation of the actuator mechanism 200 and actuator release mechanism 300 will now be reviewed. Starting with FIG. 6, the apparatus is in the ready-to-fire position with mouthpiece 20 already rotated by the user into the open position. Compression spring 210 is maintained in compression between chassis 400 and rotary cam 230. Torsion spring 220 is maintained in torsion between chassis 400 and rotary cam 230. Trigger pin 312 is positioned underneath release ring 233 and is seated in groove 236 with spring metal edge 324 engaged with lead screw 322 and return spring 326 in light compression. Driver 240 is positioned with bottom surfaces 248 flush against disk 35 which is flush against bottom 34 of canister 30, without depressing valve stem 32, and drive lugs 242 are partially inserted in notches 49. Protrusion 41A is positioned in annular recess 405 in the open position and locked in position by latch 39 so that cassette 4 will not fall out of chassis 400, receptacle 520, and body 2. The action of rotating cassette 4 to the open position places location mark 44 in a position that is sensed by contact switch 460 secured to chassis 400. This actuation is sensed by control electronics 50 and used to power up the electronics of device 6. A second microswitch (not shown) also is used to determine whether or not a cassette 4 is inserted in receptacle 520.

To release a dose, control electronics 50 monitor the user's inspiratory flow, as described elsewhere, and determine when a provided delivery threshold is satisfied. When this occurs, motor 321 is actuated to rotate lead screw 322 to allow plate 328 to retract to a first stage position. This is shown in FIG. 7. The position may be controlled by rotating lead screw 322 a selected number of revolutions or preferably by using a contact switch 327 which is positioned to be contacted by plate 328 and shut off motor 321 in response to such contact. The latter is easier to implement.

During this movement, plate 328 moves away from canister 30 a first distance (as levers 314 and 315 pivot in response to the pressure exerted on trigger pin 312 by release ring 232). The first distance is selected so that tip 313 of trigger pin 312 slides out from groove 236 under release ring 233 and into ring slot 234. When this occurs, cam 230 is no longer supported by trigger pin 312 and is translated downwardly by releasing compression spring 210. Accordingly, drive surfaces 246 also are pressed downwardly and press canister body 31 relative to valve stem 32 to release a dose of aerosol medication. However, cam 230 is prevented from rotating under the force of torsion spring 220, which is still in torsion, because trigger pin 312 is held in slot 234. Torsion spring 220 does, however, exert a force to bias release ring 233 slot 234 against trigger pin 312 and maintain spring metal 323 edge 324 pressed against the vertical thread wall of lead screw 322.

At the time motor 321 is stopped with trigger pin 312 in the first stage location, i.e., engaged in release ring slot 234 with canister 30 valve stem 32 fully depressed relative to canister body 31, control electronics 50 starts a timer. The timer controls how long motor 321, and hence trigger pin 312, is maintained in the first stage position. The time period is selected to be long enough to be sure that the desired dose of aerosol is released from canister 30 in its selected form, namely, dry powder, liquid or gas aerosol through the nozzle 22.

Figure 8:
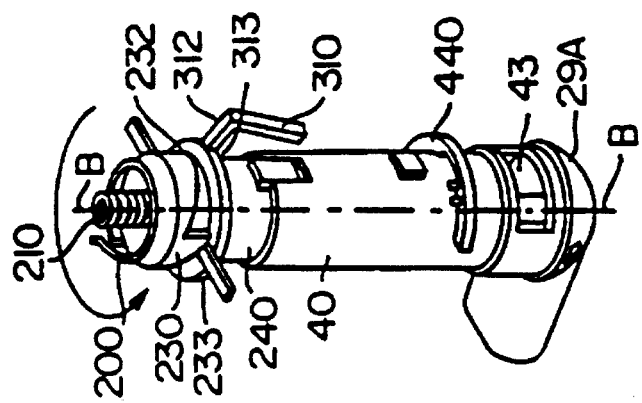
FIG. 6–10 are cutaway elevated perspective views of a sequence of the actuator mechanism and actuator release mechanism cycle for releasing a dose of aerosol medication.

At the end of the selected time period, which may be controlled by a timer (more preferably a programmable value in a microprocessor controlled device), motor 321 is again advanced to allow plate 328 to react further under the force exerted by ring slot 234. This allows lever 314 and lever 315 to rotate further and trigger pin 312 to be urged out of slot 234 because of the opposing angled faces of trigger pin 312, side face 341 and slot 234. This is shown in FIG. 8. The further advance of the motor may be limited by another contact switch or by a set time period corresponding to a given number of rotations and, hence, distance of travel of member 324 along lead screw 322.

When trigger pin 312 slides out of slot 234, torsion spring 220 releases (in this case it unwinds). Because torsion spring 220 produces more force than compression spring 210, release of torsion spring 220 causes rotary cam 230 to rotate.

As rotary cam 230 rotates, its upper cam surface 232 runs against stationary cam followers 430 and raises cam 230 upwardly. As rotary cam 230 moves upwardly, it compresses compression spring 210. Rotation and upward movement of cam 230 also results in releasing valve stem 32 so that canister 30 is closed to the atmosphere.

In the preferred embodiment, wherein canister 30 is a metered dose canister, this release action places canister 30 with its metered dose chamber in fluid communication with the reservoir of medication and carrier or aerosol precursor material and refills the metering chamber. The refilling occurs relatively shortly after the dose was delivered and, consequently, additional agitation of the medication and carrier or aerosol precursor prior to refill is not required. Thus, cam 230 comes to rest in its uppermost position, with cam followers 430 at one end of cam surface 232, torsion spring 220 released, compression spring 210 compressed, and metered dose canister 30 with a filled metering chamber and ready for delivering the next dose.

Advantageously, in the present invention, the helical torsion spring 220 is used to recock compression spring 210, by transferring its energy thereto without requiring the user to perform any operation. It should be understood that a more complex spring could be used in place of compression spring 210 and torsion spring 220, so that release of trigger pin 312 will transfer the energy that had been stored by a prior rotating cocking event to be stored in the axial compression component, for later use in depressing canister 30 for releasing the next dose. It also should be understood that the direction of rotation about axis B for the various operations described herein maybe clockwise or counterclockwise, with appropriate mirror image parts and angles being usable.

Figure 9:
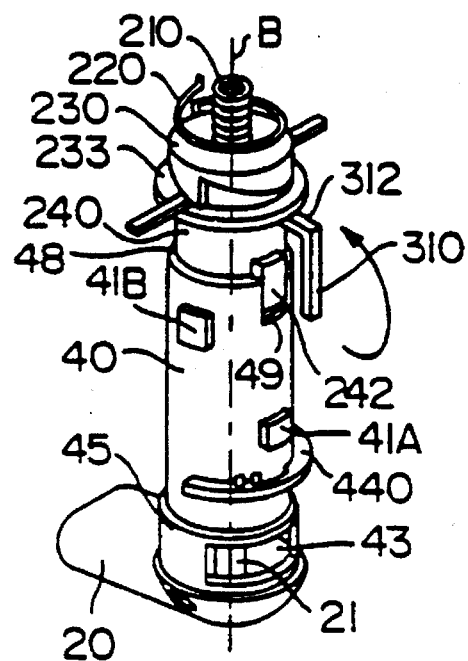

Referring now to FIG. 9, after trigger pin 312 slides out of slot 234, motor 321 continues to advance for a period of time, e.g., 0.5 to 2 seconds, or for a number of revolutions, that is sufficient for cam 230 to rotate upwardly on cam followers 430. In this regard, the uppermost position of cam 230 is high enough so that when return spring 326 releases, it drives plate 328 along guide rod 325 back to the initial ready-to-fire position and returns trigger pin 312 to a pre-ready-to-fire position positioned underneath release ring 233. In this condition, compression spring 210 is compressed, torsion spring 220 is released, and rotary cam 230 is held in its uppermost position by cam followers 430 over trigger pin 312.

Figure 10:
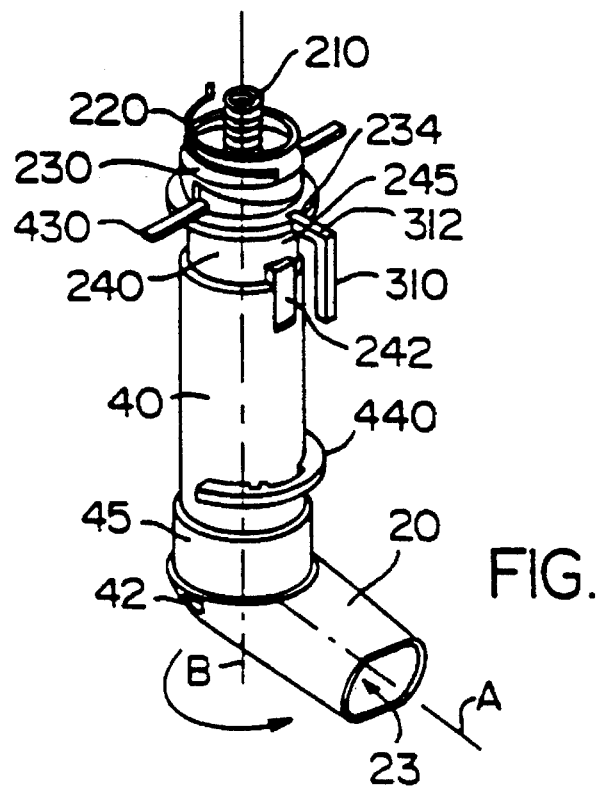
Figure 11:
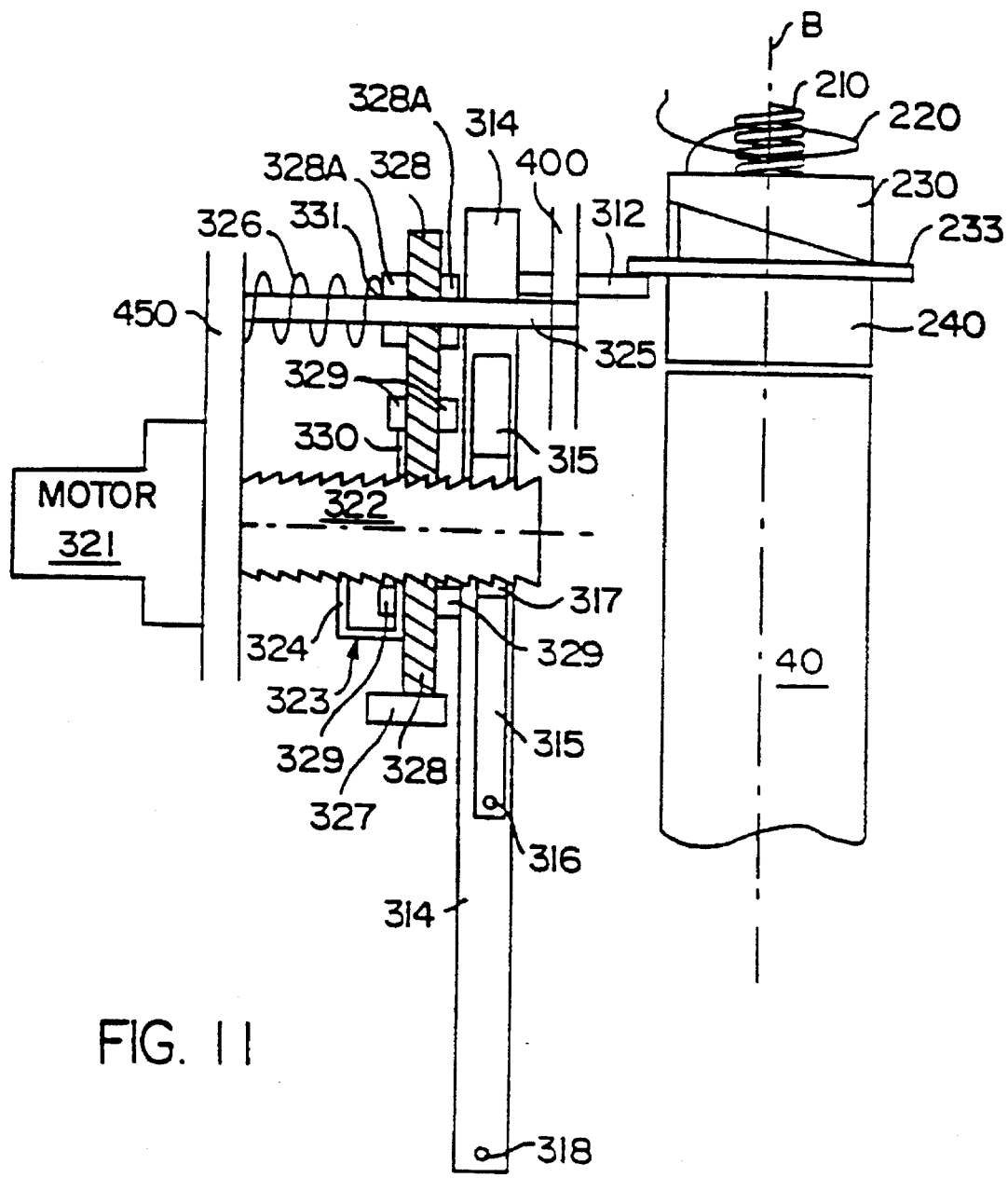
FIG. 11 is a side partial section view of the actuator release mechanism of FIG. 3.

The pre-ready-to-fire condition is followed by a cocking operation, which places device 6 in the ready-to-fire condition. With reference to FIG. 10, the cocking operation is performed by rotating cassette 4 into the closed position. As a result, one of the drive dogs 245 of driver 240 engages protrusion step 239 at the bottom of rotary cam 230 and causes cam 230 to rotate. This rotates cam 230 relative to cam followers 430. As a result, cam 230 will move downwardly on cam surface 232 as it rotates until it is supported by trigger pin 312 acting on the release ring 233. At that point, cam 230 will continue only to rotate until groove 236 of release ring 233 is again engaged with the top surface of trigger pin 312 and places cam followers 430 at the other end of cam surface 232. The engagement occurs at less than about 10° from the fully closed position (0°). When the user releases cassette 4 after it is fully closed, torsion spring 220 will tend to release. This results in slot 234 acting on trigger tip 313, which also inhibits rotation. This locks torsion spring 220 in torsion. Thus, device 6 is ready to be opened for delivering aerosol medication.

Because mouthpiece 20 has a length of about 1.38 inches (35 mm) from the center of rotation (Axis B), the patient has sufficient leverage to rotate cam 230 and place torsion spring 220 in torsion, with sufficient force to drive cam 230 to compress spring 210 after the next delivery of medication. Preferably, compression spring 210 stores on the order of 8 pounds (3.629 kg) which is sufficient to depress valve stem 32 when spring 210 is released. Torsion spring 220 preferably stores on the order of 0.9 pounds-inches (1.0 kg-cm) which is sufficient to compress compression spring 210 after the release of a dose of medication.

It will be appreciated that the present invention also can be practiced by variations of the mechanical structure described above. For one example, it is possible to use a release ring 233 which does not have a groove 233. In such an embodiment, trigger pin 312 is used to engage slot 234 to prevent torsion spring 220 from releasing and to rest underneath release ring 233 to prevent compression spring 210 from releasing. The advantage of this structure is that the distance of travel of cam 230 along axis B for depressing canister 30 and for reinserting trigger 312 under release ring 233 is increased by the depth of groove 233, e.g., 0.015 inches. In such an embodiment, the angular configuration of trigger tip 313 may be modified if necessary, to provide the required clearance as well as the restraining and ejection functions.

For another example, it is possible to replace compression type release spring 326 with a helical torsion spring that is mounted about pivot 318 and to provide pusher plate 328 with a flange that hooks onto secondary lever 315 (not shown). In this embodiment, the torsion spring is used to act on primary lever 314, which in turn will pull secondary lever and plate 328 towards canister 30 for resetting trigger pin 312 under release ring 233 when the forces pressing plate 328 towards motor 321 are removed. Yet another variation could use a torsion spring secured about secondary lever 315 pivot 316.

The use of a compound lever 314, 315 minimizes the force requirements of motor 321, spring member 323, and return spring 326. This is important in reducing the energy consumption requirements for a battery powered hand held device. Indeed, the consumption requirements are reduced further by operating the motor as a controlled brake resisting the forces exerted by springs 210 and 220 and turning the motor off to act as a passive brake, except when a controlled retraction of trigger pin 312 is to occur. During the time motor 321 is stopped in the first stage position, it does not consume energy. Advantageously, motor 321 can run directly off battery 60, which simplifies the power supply circuitry and minimizes the bulk of device 6.

Another advantage of the present invention is that it provides opening mouthpiece 20 as a passive event, whereby it requires little effort. It also obviates the need for the patient to have to cock the device immediately prior to use. This can be important to patients who are in distress or suffering a severe asthma attack and who might in panic forget or be unable to cock a device.

The time that motor 321 is maintained in the first stage, with valve stem 32 depressed relative to canister body 31, can be selected and controlled by control electronics 50. Accordingly, the present invention is particularly useful with canisters, valve stem receptacle flow paths, and/or nozzles that have relatively slow or long release times, i.e., the time that the valve stem must be depressed to maintain open the metering chamber (for a metered dose inhaler) or a straight valve canister to release the proper dosage of aerosol medication. In this regard, most available metered dose inhalers have a release time on the order of 90–100 msec, such that the valve stem must be held down for about one-tenth second to ensure complete release. This is easy for most individuals to achieve. Slow release valves may have a greater release time, e.g., on the order of one-quarter second, three-quarter seconds, two seconds, or more. The release time of this length is more difficult to achieve manually on a reliable basis.

Advantageously, the present invention is able to deliver medications formulated to have long release times which heretofore could not be used in a metered dose inhaler because of the difficulty of providing the required release time. This feature also is particularly useful with straight valve canisters and dry powder delivery systems where the release time controls the amount of medication released.

Referring to FIGS. 1–3, 16A–H and 17A–C, durable body 2 may be formed of a left half 11, a right half 12, and an airway cover 13, which provide a portable, hand held device. Body 2 also includes a display 510, preferably mounted in one of housings 11 and 12. Enclosed inside housings 11 and 12 are one or more batteries 60, actuator mechanism 200, actuator release mechanism 300, (which may include a motor 321) chassis 400, control electronics 50, a receptacle 520 for receiving cassettes, and flow transducer 600.

Display 510 may be a liquid crystal display (LCD) device for displaying alphanumeric characters of measured flow or pulmonary function parameters, or instructions to the patient for using device 6 under microprocessor control. The LCD display may display quantitative or qualitative measures. One such LCD display 510 is a custom part model No. 0219-3211-F14 available from DCI, Olathe, Kans. It provides for display, in response to software programming, of one or more of shot count of released (delivered) and/or remaining doses of medication, a low battery indication, a warning icon, e.g., "consult your doctor," three arrows to indicate inadequate, nominal or acceptable pulmonary function, annunciations for total exhaled volume, peak flow and annunciations indicating the day of week, time, month and year.

The display features of device 6 also may include a light emitting diode (LED) array 510' for indicating various parameters, for example, (1) that the device is on, (2) ranges of determined breath flows, e.g., good flow corresponding to successful delivery, bad flow corresponding to aborted delivery, (3) a qualitative measure of a measured pulmonary function, e.g., normal, nominal, and abnormal, and (4) relative changes in measured pulmonary function, e.g., improving the same degrading conditions. LED array 510' may include three LED devices, e.g., green, amber and red (or three of the same color), and appropriate labeling printed on housing 11 or 12. A selector switch also may be provided to indicate which parameter is being displayed on array 510'.

Control electronics 50 preferably includes a microcontroller device including a microprocessor, RAM and ROM memory, and buffers, and also includes external analog-to-digital converters, latches, RAM/ROM memory, and signal conditioning circuits for receiving and transmitting signals in and out of control electronics 50, in digital and/or analog form. Such devices include a model 68HC11D3 microcontroller available from Motorola, analog to digital converter part No. AD7701 available from Analog Devices, and interface amplifier model No. AD22050 available from Analog Devices for conditioning the signal from the pressure transducer for digitization.

The microcontroller, memory, and analog-to-digital converter must have sufficient capability and processing speed for processing the output signal produced by flow transducer 600, convert the output signal to the flow rate signal and, in accordance with selected protocols, derive a flow value signal from the sensed flow rate for causing actuator release mechanism 300 to release a dose of aerosol during inspiration of the patient and determine pulmonary functions based on the acquired flow signals. A suitable sampling rate is greater than 60 Hz, e.g., 75 Hz, for analog to digital conversion and processing.

Chassis 400 is secured to one or both of housings 11 and 12 such that it is adjacent an interior receptacle 520 for receiving cassette 4. Mounted to chassis 400 are cam followers 430, keyplate 440 for receiving only cassette 4 having protrusions 41 that correspond to the plurality of slots cut in keyplate 440, motor mount 450 for mounting actuator release mechanism 300, annular recess 405 and contact switch 460 for sensing the presence of location mark 44 on cassette 4 indicating that cassette 4 is fully rotated to the open position. Chassis 400 is securely mounted to body 2. Receptacle 520 includes a first section that receives the upper part of housing 40 and a second section that receives the lower part 45 of housing 40. A ledge 447 separates the upper and lower receptacle sections and receives bearing surface 47 of cassette 4. Contact switch 462 is used to indicate that cassette 4 has been inserted in the receptacle adjacent to chassis 400.

Figure 16D:
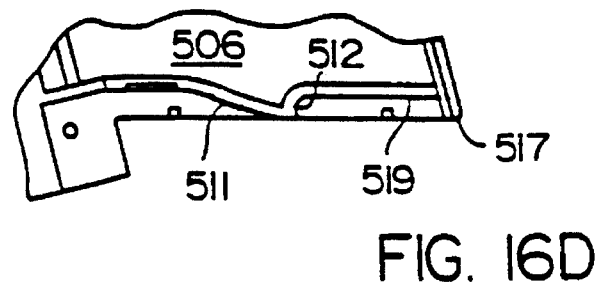
FIG. 16D is an enlarged view of the flow sensor surface of the embodiment of FIG. 1.
Figure 16E:
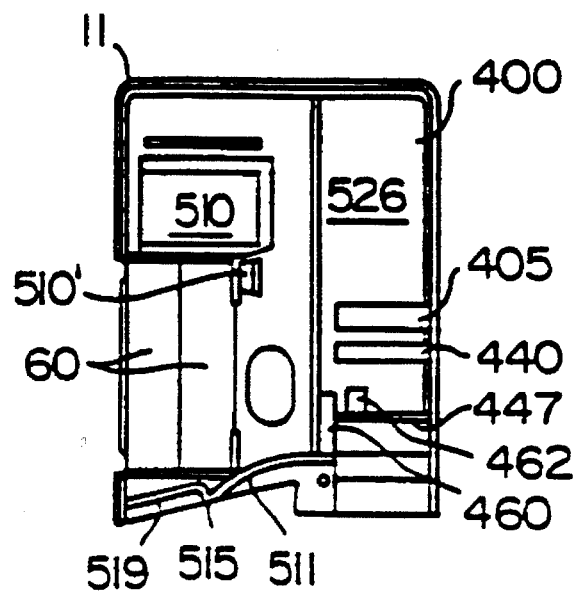
FIG. 16E, 16F, and 16G are respectively side, top and bottom view of the other housing of the durable body of FIG. 1.
Figure 16F:
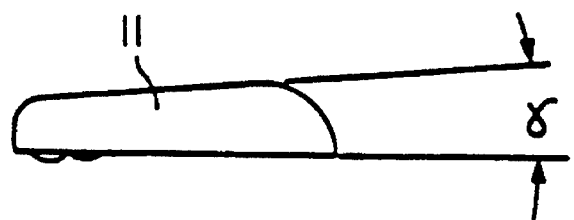
Figure 16G:
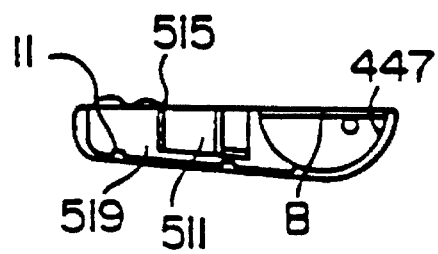

Referring to FIGS. 16A through 16H one suitable form of the durable body 2, excluding airway cover 13, is shown. With reference to FIG. 16E, housing 11 is shown with receptacle 520 for receiving cassette 4 having annular recess 405 and keyplate 440 is shown. This embodiment includes two batteries 60 and LCD display 510 and LED array 510' within housings 11 and 12.

With reference to FIGS. 16B, 16C, 16E, and 16F, body 2 is provided with a contour that is easy for the patient to hold securely. The larger side planar walls of housing 11 and 12 are each angled at an angle of about 4.5°. It should be understood that alternate configurations of housings 11 and 12 could be used.

Referring to FIGS. 3 and 17A–17C, airway cover 13 connects to the bottom of body 2, more specifically, housings 11 and 12, after they have been secured together. Airway cover 13 includes ports 507 at the larger end distal to the patient's airway, and has a curved edge 501 in a horizontal plane at the proximal end, adapted to receive the perimeter of region 29A of top end opening 29 of mouthpiece 20. This allows mouthpiece 20 to rotate and maintain a close fit with the airway between airway cover 13 and the bottom of housings 11 and 12. In addition, airway cover 13 is provided with a corner surface bend indicated by 509, which receives the mouth end 25 of mouthpiece 20 when cassette 4 is rotated to the closed position. This provides a neat outer appearance and a relatively smooth surface for durable body 2, which makes its convenient to carry in a pocket or pocketbook. It also provides a convenient mechanism for blocking the open end 23 of the airway so that material is not lodged in the flow path. It also eliminates the need for a separate cap to cover the opening. The distance between the flat wall section designated 508 of airway cover 15 and the bottom of housings 11 and 12, designated as wall 506, is on the order of 0.38 inches (9.65 mm) and a width of 0.90 inch (22.86 mm) at the maximum dimensions. The side walls taper at nine degrees, 4½° per side, to follow the outside of housing 11 and 12. Although these dimensions are not critical, they must be sufficiently large to provide for a flow path between mouth end 25 of mouthpiece 20 and apertures 507 of airway cover 13 when mouthpiece 20 is rotated in the open position and provide a detectable pressure difference between pressure tap 516 and atmospheric pressure while maintaining an acceptable air flow.

Referring to FIGS. 3, 16D, 18B and 18C, flow transducer system 600 includes a pressure transducer 505, a durable flow measurement section having a contoured surface built into wall 506 at the bottom of housings 11 and 12, airway cover 13, and a pressure port 516. Preferably, the contour of wall 506 is flat in the cross section end view as shown in FIG. 18C. Airway 601 mates with the airflow path 24 (through mouthpiece 20 end 23 and top end opening 29 the lower portion of 45 of housing 40, and out aperture 43). Airway 601 comprises the bottom wall 506, made of the mated housings 11 and 12, and airway cover 13.

In operation of the present invention, as the patient inhales or exhales through the device, flow through path 601 is sensed at pressure tap 516 in wall 506 and at atmospheric pressure (not shown) by pressure transducer 505. The output signal of transducer 505 is converted to a digital value by control electronics 50 at a selected sampling rate and integrated at that sampling rate to obtain inhaled or exhaled volume. Drug dispensation timing and therapeutic decisions are based upon these measurements of flow rate and volume.

Airway cover 13 is removable to facilitate cleaning of the durable flow measurement section. It has a rectilinear wall section 508 which defines a cross sectional area with opposing wall 506. Wall section 508 has a corner 509 which opens out at almost a 90° angle to provide a larger dimensioned chamber 550. The distal end of chamber 550 has apertures (ports) 507 for air flow therethrough without any significant pressure drop across apertures 507. The type of opening is not critical as long as chamber 550 allows the flow into the chamber to expand. Hence, a 90° bend is convenient, but not required.

Wall 506 has at the proximal end a tapered lead-in section which includes a ramp indicated by reference 511. Ramp 511 reduces the cross-sectional area between walls 506 and 508 at the beginning of ramp 511 (indicated by reference 513) to a minimum cross sectional area at orifice throat 515. Wall 506 includes an undercut portion 512 under throat 515, which connects throat 515 to a wall segment 519, is in the same plane as wall 506 proximal to ramp 511 and provides about the same cross sectional area as at the beginning of the ramp 511.

Walls 506 and 508 are thus constructed to form an asymmetrical structure that comprises elements of a pneumatic diode, a fixed orifice flow meter, and venturi port flow meter. A pneumatic diode is a structure that presents one flow resistance as the air passes in one direction across the surface and a different flow resistance as the air flow passes in the reverse direction. A fixed orifice meter is one that presents an orifice in the path that is generally symmetrical with the airflow path, but of smaller dimension. Flow through the orifice creates a differential pressure across the orifice which can be measured by sensing the pressure on either side of the orifice in a conventional manner. It is noted that the sides of airway cover 13 could be made straight, rather than tapered. If so, then the cross sectional area between throat 515 and wall 508 must be accordingly adjusted to provide the same orifice area as when the side walls are tapered.

The orifice meter principle is simple. In order to generate a flow through an orifice there must be a pressure difference across the orifice. If there is no pressure difference then there will be no flow. Likewise, if there is a flow across an orifice, there will be a pressure differential that can be measured.

The flow rate, Q, is dependent on a string of constants, the square root of the inverse of the air density and the square root of the difference in pressure across the orifice.

$$Q_{actual} = KA_2 \sqrt{\frac{2q_c}{\rho}} \sqrt{P_1 - P_2}$$

The terms K and A are constants dependent on the system geometry and $g_c$ is a dimensional constant. In the present invention, only the pressure on the patient side of the orifice and the atmospheric pressure are measured.

The flow rate vs pressure drop curve is parabolic. Therefore, it would require a huge dynamic signal range to detect the small pressures generated at near zero flows and also not peg the system signal during high flow rates. The low flow rate sensitivity in one direction is required to measure accurately inhale maneuvers, which typically range from 0–200 liters per minute. The large flow rate range in the other direction is required to measure the high flow rates during, e.g., a forced exhale maneuver which typically range from 0–800, more preferably 0–720, liters per minute. The latter are used to measure a pulmonary function.

It has been discovered that, by using an asymmetric orifice, instead of the usual symmetric orifice, such different ranges of flow rates can be effectively measured by the same flow transducer over a relatively full scale for maximum signal resolution in the different ranges.

When the device is in inhale mode, the flow is developed by reduced pressure at the patient side, drawing air over undercut 512 of wall 506. In this mode, wall 506 behaves essentially like an orifice meter, except that there is a back eddy created by undercut 512. The back eddy helps increase the flow resistance in the inhale direction, thus adding to the total differential pressure.

On exhale, there is a different effect. The flow encounters a smooth transition along ramp 511 to the orifice throat 515, which requires a certain amount of pressure to push it through. The pressure required is about 40% as much as for the same inhaled flow rate. The pressure sensed, however, depends on the position of pressure tap 516 in wall 506. If pressure tap 516 is placed at location 518 as illustrated in FIG. 18A, then the difference between exhaled and inhaled sensed pressures (for same flow rate) is about 2:5. If pressure tap 516 is placed on ramp 511 as illustrated at 518' in FIG. 18A, then there is additionally a venturi effect that comes into play. In this regard, as the flow rate increases, there also is a pressure drop that is superimposed upon the pressure required to generate the flow. The venturi effect is also parabolic with respect to flow rate. The relative position of pressure tap 516 on ramp 511 determines the magnitude of the venturi effect. This allows for varying the difference between the exhaled and inhaled sensed pressures ranges from between 2:5 and 1:100 or more, based on careful selection of the location of pressure tap 516 on ramp 511. The venturi effect can be made strong enough so that sensed pressure can go negative with respect to atmospheric pressure at exhaled flow rates by placing pressure tap 516 very near the orifice throat 515.

As a result, wall 506 of the present invention yields a structure where sensed pressure resulting from a flow in one direction can be radically different from sensed pressure from the same magnitude flow in the other direction. The inhaled flow rate vs. pressure drop curve depends mostly on the selected size of the orifice, i.e., the distance between throat 515 and wall 508, and somewhat on the shape of undercut 512. It also depends on pressure tap 516 position on ramp 511. The exhale curve also depends on orifice size, but is radically changed by the position of pressure tap 516 along ramp 511 relative to the venturi throat 515. This allows for measuring flow rates in both directions using the full range of the transducer in each direction, even though the maximum flow rates have different magnitudes.

Referring to FIGS. 3, 16D, and 18B, in one embodiment, the distance between throat 515 and wall 508 is 0.185 inches (4.69 mm). The dimensions of undercut 512 is a radius of 0.067 inches (1.7 mm) having a centerpoint that is about 0.745 inches (18.9 mm) from backwall 517. Backwall 517 is part of the durable body 2 and interconnects with the backwall of airway cover 13 that includes apertures 507. The thickness of wall 506 at the throat 515 is approximately 0.161 inches (4.24 mm). Ramp 511 is comprised of two cylindrical segments having opposite curvatures. The first curve begins tangential with wall 506 at end 513 has a radius of about 0.732 inches (18.6 mm) from a centerpoint spaced 0.6 inches (152.4 mm) from the orifice throat 515, perpendicular to wall 506 and wall 508. The other curvature, which terminates as orifice throat 515, has a radius of about 0.791 inches (20.09 mm) having a centerpoint spaced 0.78 inches (19.8 mm) from throat 515 on the other side of wall 506.

Pressure tap 516 is preferably a circular hole that extends through wall 506 and terminates in ramp 511 facing wall 508. Pressure tap 516 is preferably normal to the surface of wall 506 in which it terminates and spaced to one side or the other of the midplane as illustrated in FIG. 18C. The precise location of pressure tap 516 is a matter of design choice for the particular use of the device. Pressure tap 516 is connected to transducer 505 by a flexible plastic tube 550, e.g., PVC. The PVC tube need not have the same diameter as tap 516. The diameter should not be so small as to wick moisture, e.g., $\frac{1}{32}$ to $\frac{1}{16}$ of an inch inner diameter. The orifice of pressure tap 516 will be about 0.030 inches.

In the present invention, the pressure versus flow rate curve along flow path 601 is typically non-linear in both directions. Applicants have realized that it is impractical to design and construct a flow path 601 with precise dimensions to obtain a flow having linear pressure vs flow rate characteristics.

A problem with using linear devices is that they are too bulky for a handheld, portable device and typically contain screens or other orifice arrays which become clogged or plugged during use and need to be cleaned or replaced to avoid inaccurate measurements. However, applicants also have realized that a linear relation is not required and can be dispensed with by calibrating the flow path 601, as actually built, to produce from the actual sensed flow calibrated data. Moreover, by providing flow transducer system 600 as part of durable body 2, applicants have realized that only flow path 601 needs to be calibrated, and not flow path 24. This further simplifies construction of mouthpiece 20 and cassette 4, and avoids the need to maintain tight tolerance controls for the construction of those other parts. In this regard, the measurement made is not the pressure drop through the entire system flow paths 24 and 601, which might be changed slightly by minor variations in cassette 4. Rather, the pressure drop measurement is obtained only across the flow path 601 between housings 11 and 12 and airway cover 13, and hence is independent of minor variations in cassette 4. Further, total pressure drop through the entire system is also mostly independent of cassette 4 manufacture variations between the orifice 515 in the flow measurement section is substantially smaller and thus more restrictive than the port 23 and mouthpiece 20 in cassette 4.

Accordingly, in accordance with the present invention, a calibration look-up table is derived and stored in nonvolatile memory of control electronics 50 for each body 2. This provides for measuring a flow dependent pressure signal, i.e., the voltage signal output from transducer 505 and looking up the corresponding calibrated flow value. In one embodiment, the look-up table is a selected number of data points long, e.g., 59 points. The look-up table may be considered as two arrays or, tables, each having 28 data points for flow in each direction and sharing the zero flow rate.

Control electronics 50 thus obtains the flow dependent signal, applies the obtained value to the look-up table, and performs piecewise linear interpolation between the points in real time so that it can measure rapidly changing flow rates. The calculated flow values are then integrated to determine volume or used to measure a pulmonary function, as the case may be. The look-up table is generated during the calibration of each device 6. Although in the preferred embodiment the valid flow values, i.e., values above a selected noise threshold, are always integrated, in an alternate embodiment, integration need not occur unless a flow volume is required.

In a preferred embodiment, an automated calibration routine is used to determine the look-up table.

First, the uncalibrated durable body 2 is placed on a fixture that terminates in a dummy disposable cassette 4, the same way that a patient's drug cassette 4 would be inserted into the device. Second, a known air flow is introduced through the durable flow path 601 by a calibrated flow controller. Third, the flow rate and transducer 505 response to a known flow are recorded by a computer (not shown). Further, the flow rate is adjusted to the next flow level by the flow controller, and the second and third steps 2 are repeated for, e.g., up to 59 different flow rates in the two flow directions. Fifth, the recorded data is transformed into a calibration table and may be run through a curve fitting routine to look for outlying or bad data points. Those points, if any, are remeasured. Alternately, a curve fitting routine may be used to find the best fit through the data prints to a desired degree of accuracy, e.g., 2nd order. Sixth, a calibration table is then generated and downloaded into the RAM memory of control electronics 50. The table may be the raw data or curve fit data points. The calibration is then spot checked at several flow levels to assure proper loading of the table. A check sum is also stored in memory with the calibration table so that the look-up table can be checked for corruption each time the device 2 is turned on.

A preferred flow sensing transducer 505 used to measure these pressure changes is a resistive strain-gauge type device having two ports. One port is vented to ambient pressure. The other port is connected by tube 520 to the pressure tap 516 which is located within airway 601, preferably on ramp 511 (see FIG. 18c). Pressure changes at the airway port 516 cause the resistances within sensor 505 to change. These resistance changes are provided in the form of a variable voltage output which is digitized by control electronics 50. The digital value is converted to a corresponding flow value using the predetermined calibration look-up table stored in the system memory PROM, ROM, or nonvolatile RAM. One suitable transducer 505 is model NPH-8-002.5DH, available from Lucas Novasensor, Fremont, Calif.

Pressure sensors 505 of this type are known to suffer from several problems. First, the devices exhibit thermal and long-term drift, causing the output signal to wander slightly after power-up. The output signal also varies with the orientation of the sensor. Normally, these effects would be negligible. However, in the application of the present invention, the parabolic nature of the flow-pressure curve makes the accuracy of look-up table conversion very sensitive to these offset changes. This is because, at low flow rates, a very small change in the pressure signal maps into a relatively large change in the calculated flow rate.

For example, it was discovered that if the offset of the pressure signal was only measured at power-up and if the orientation of the transducer changed or if device 6 was left on for more than a few minutes, erroneous flow rates of up to ±30 liters/minute would often be reported. Accordingly, it was realized that the offset would have to be monitored and accounted for. The simple approach is to linearize the flow-pressure curve (either mechanically or electronically) to eliminate this problem. However, as already noted, this effort proved to be unfeasible and unnecessary.

As realized by the inventors, because the sensitivity of the system to changes in the offset of the pressure transducer cannot be easily reduced to an acceptable level, the magnitude of the offset changes must somehow be lessened. Specifying tight tolerances for drift and orientation sensitivity would make transducer 505, or control electronics 50, prohibitively expensive. The inventors realized, however, that a cost effective solution is to measure and correct for offset changes as they occur in real time. The inventors also realized that it is important to correct for zero-flow offset changes during zero-flow conditions and that this presented a different problem of determining when zero flow conditions occur even in the face of drift offset.

The inventors discovered that the inherent noise of the unfiltered digitized signal during a zero-flow state is about ±2 A/D counts. The inventors discovered that even at low flow rates, when the sensitivity to flow variations is low, maintaining an airway flow rate which produces a pressure signal constant to within ±2 A/D counts for any length of time is virtually impossible. Therefore, they realized, a pressure signal remaining constant for a relatively long period of time is indicative of a zero-flow state. This criterion was accordingly selected and used to determine appropriate times to measure and modify the zero-flow offset value.

The method assumes that any drift occurs slowly enough not to influence the peak-to-peak variance calculated over the specified time period, and that orientation changes are transient events.

According to a preferred embodiment of offset correction, the device maintains a buffer holding the last 25 A/D values, which corresponds to ⅓ of a second of pressure data. The A/D values are the digitized output of pressure sensor 505. After a new data point is placed in this buffer, the difference between the minimum and maximum values in the buffer is calculated. If the calculated difference is less than or equal to three, then the system concludes that a zero-flow condition exists, and a new offset is calculated.

To calculate the new offset, the mean value of the 25 values stored in the buffer is first calculated. The difference between this calculated average, representing the current zero-flow reading, and the base value for this zero-flow signal is calculated. This difference is then stored as a new A/D offset term. If each direction of flow is to have a symmetrical range of A/D counts, then, the base zero flow condition is the midpoint of the A/D range, e.g., zero for a bipolar A/D converter, or 32768 for a 16-bit unipolar A/D converter.

The offset drift correction aspect of the present invention will be better understood by the following example. On power-up initialization, the system measures an average zero-flow pressure signal of 30000 A/D counts. The range of the unipolar A/D converter is 0-65535 counts, corresponding to an input range of 2.5 volts, such that each A/D count is 38 μV. For a symmetrical A/D count sample, the ideal base zero-flow signal is thus:

$$\frac{65535}{2} = 32768 \text{ counts.}$$

The A/D offset term is then calculated to be:

30000−32768=−2678 counts.

The offset term is subtracted from all subsequent A/D measurements before these readings are mapped into flow values using the look-up table.

After some operating time, the pressure transducer output drifts slightly, resulting in an unadjusted average output of 31000 counts for the current zero-flow condition. When the original calculated offset of −2678 counts is subtracted from this value, an adjusted average of 33768 counts is obtained, which would normally cause a large erroneous flow to be reported. However, the peak-to-peak variance over the previous 25 values will eventually become less than 4 A/D counts. At this point the system will assume a zero-flow state exists and computes a new offset term to be:

31000−32768=−1678 counts.

A subsequent unadjusted pressure reading of 31000 counts will now result in an adjusted value of:

31000−(−1678)=32768 counts.

Note that the new offset now compensates for the 1000 count drift in the pressure signal.

Figure 20:
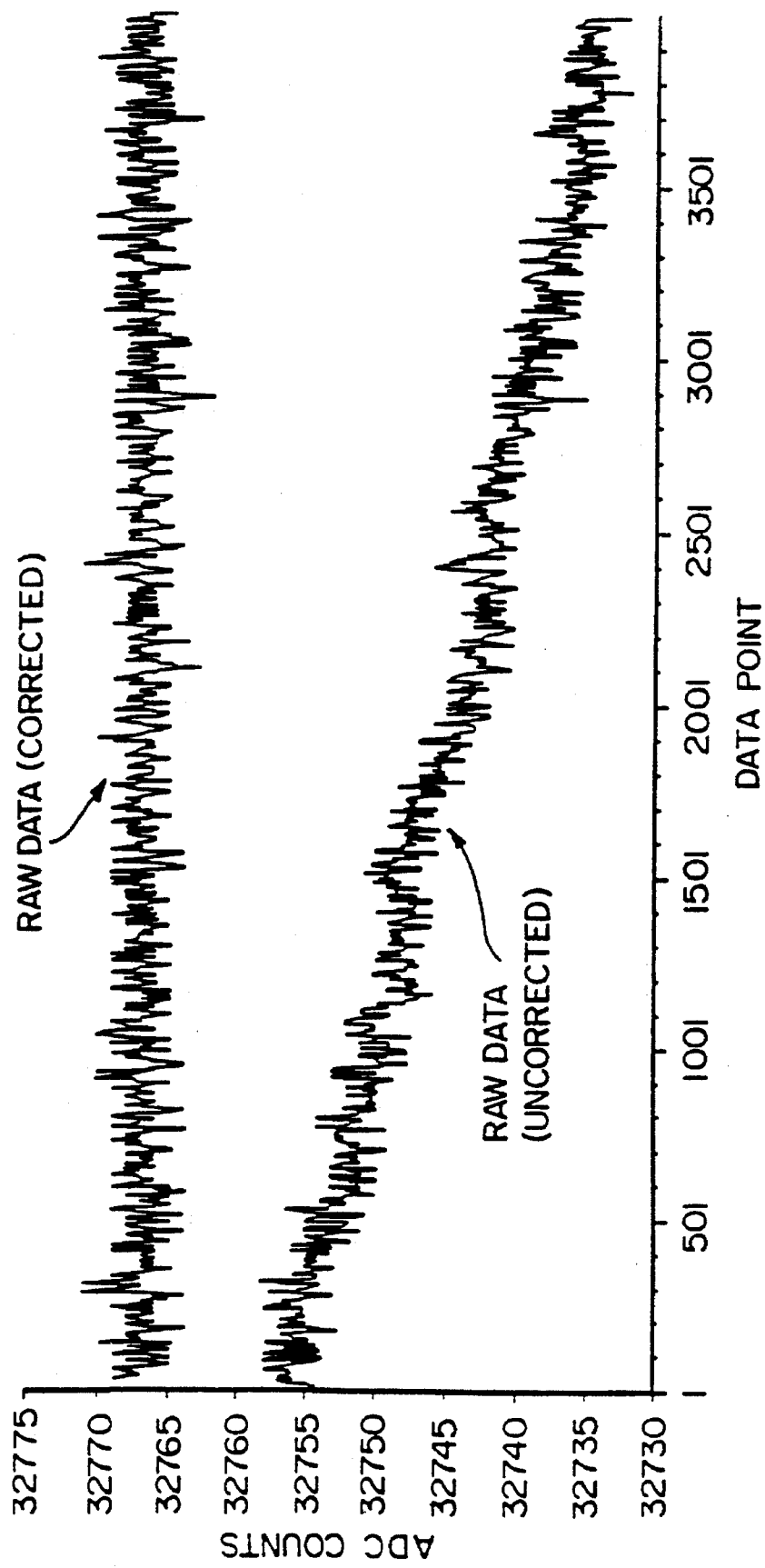
FIG. 20 is a plot of analog to digital converter counts versus time (data points) illustrating the corrected and uncorrected flow data in accordance with offset drift correction of the present invention.

The parameters specified above have been implemented in a prototype device, and appear to work well in allowing the system to quickly compensate for offset drift and orientation changes. See FIG. 20, which is a representative plot showing in the lower curve the actual offset drift of the flow sensor over time (in number of data points, where the time interval between data points is 13.3 ms) and in the upper curve the corrected value according to the offset correction routine of the present invention. It is noted that many other combinations of filter length and peak to peak difference may work equally well. Non symmetrical ranges of A/D counts also could be used if it is desired to have either greater resolution or a greater flow range in one of the two directions. This approach also could be performed using hardware circuits as well as software controlled microprocessor signal processing.

Figure 19A:
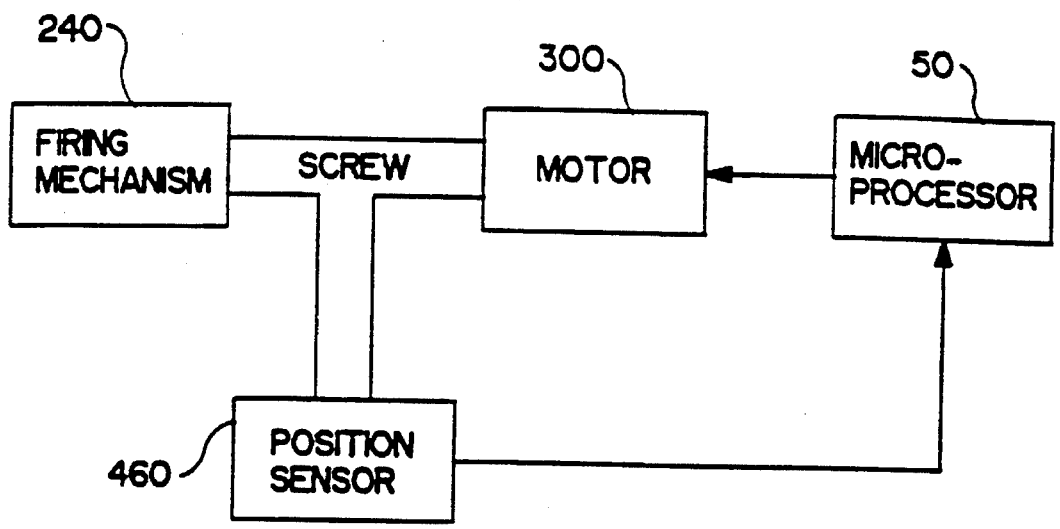
FIG. 19A is a flow chart of the operation of the actuator mechanism and the actuator release mechanism of FIG. 1.
Figure 19B:
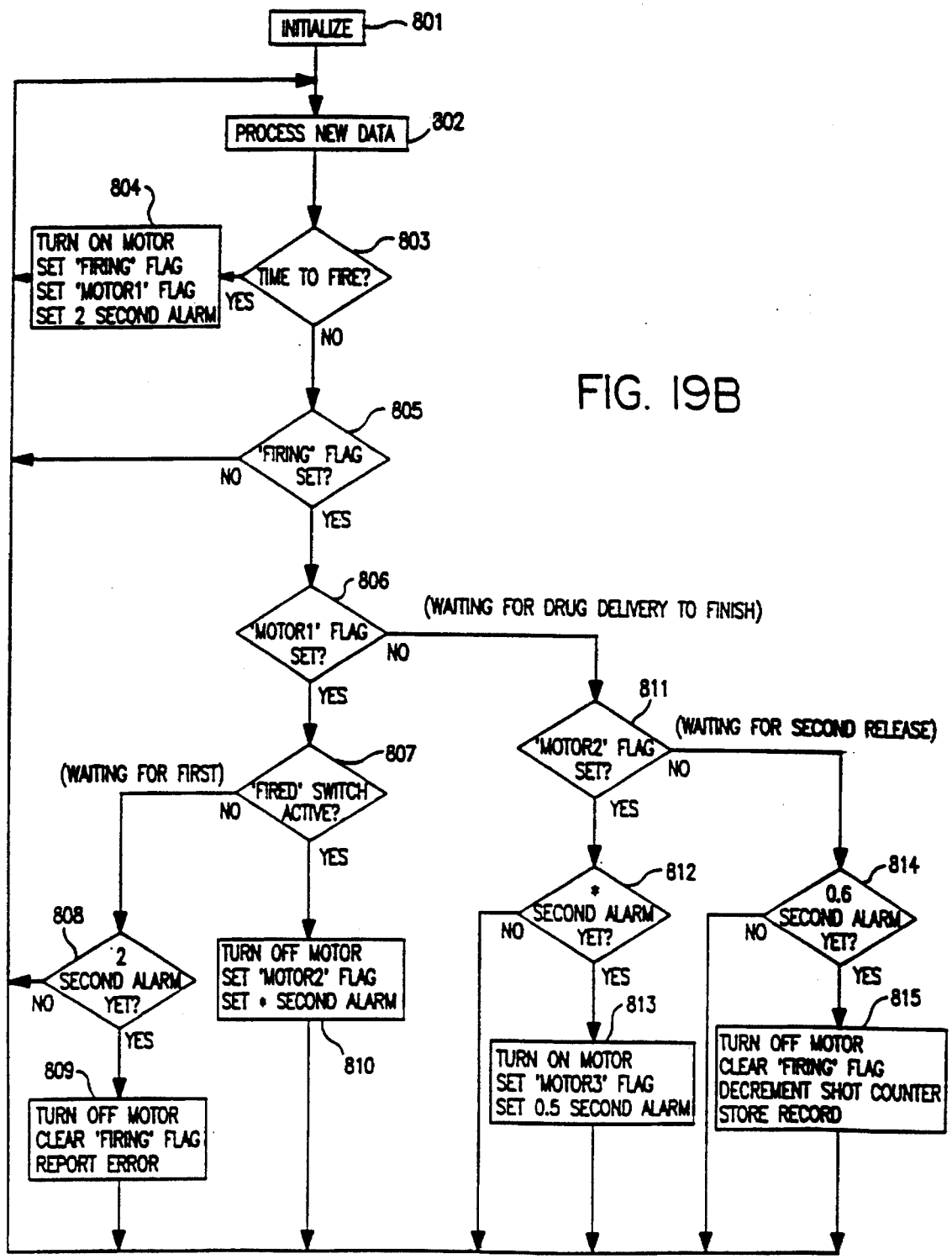
FIG. 19B is a flow chart of a process for delivering aerosol in accordance with an embodiment of the preset invention.

Referring to FIG. 19A, a block diagram illustrating the interaction of control electronics 50, actuator release mechanism 300, actuator mechanism 200, and position sensor 460, e.g., a contact switch, are shown. A flow diagram showing the essentials of a process for controlling the release of a dose of aerosol medication is shown in FIG. 19B. One suitable routine is as follows. When mouthpiece 20 is rotated into the open position, position sensor 460 senses location mark 44 and initializes the control electronics at step 801. Step 801 is followed by processing flow data, including digitizing the output signal provided by transducer 505, passing the digitized data into a buffer storage memory, mapping the acquired pressure data using the look-up table into determined flow rates, and determining current calibrated flow rate information at step 802.

At step 803, the system determines whether or not the time for releasing a dose has occurred. In this regard, the flow rate is checked to determine if it is an inhalation. If it is, the acquired flow data is compared to preselected delivery threshold parameters. For example, as previously described in detail, the flow rate is checked first to determine if it is within a flow rate range. If it is, then the flow volume information is checked to see if it is in a flow volume range. If both ranges and satisfied simultaneously, then, at step 804, motor 321 is turned on, a "firing" flag is set, a "motor1" flag is set, and a two second alarm is set. This results in the lead screw 322 rotating so that ratchet member 323 moves toward motor 321 as trigger pin 312 is urged out from under release ring 233 and into slot 234, and the processing returning to step 802 to process new data. If it is not time to fire, then the routine queries whether the "firing" flag is set at step 805. If the "firing" flag is not set, the routine returns to process additional new data at step 802. If the "firing" flag was set, then the routine checks to see if the "motor1" flag also is set at step 806. If the motor1 flag is set, then the routine queries at step 807 whether a fire active position sensor (contact switch 327) is actuated, which indicates that trigger pin 312 has moved enough to release compression spring 210 and a dose of medication. If the switch 327 is not active, then the routine passes to step 808 where the two second alarm is checked. If the alarm has not expired, the routine passes to step 802 for new data. If the alarm has expired, then at step 809 the motor 321 is turned off, and the "firing" flag is cleared. The two second alarm is used to preserve battery life. An error may be reported. Optionally, the error message is displayed on display 15. The routine then passes back to processing data step 802.

If the fire active switch 327 has triggered at step 807, then the routine passes to step 810 where the motor is turned off, a "motor2" flag is set, the "motor1" flag is cleared, and a * second alarm is set, wherein * is the programmed delay interval. The motor is then turned off for the programmed delay interval. The interval is selected to provide for complete release of the dose of medication. As noted, this time depends upon the nozzle dimensions and may be any number of milliseconds, e.g., from less than 1/10 of a second to more than 2 seconds. Importantly, this provides for delivery of medication formulations, using a timed (slow) release valve, that are not presently obtainable with conventional meter dose devices. For example, use of timed-release valves and small diameter nozzles (less than 0.018 inch) may improve the delivery of inhaled steroid formulations, i.e., reducing the amount of drug deposited into the mouth.

Following steps 808, 809, and 810, the routine returns to process new data at step 802. If at step 806 the "firing" flag is set and the "motor1" flag is not set, then the routine waits for the dose to be delivered and passes to step 811 where the "motor2" flag is checked. If the "motor2" flag is set, then the routine checks to see if the programmed delay * interval has expired at step 812. If it has not, the routine returns to process new data at step 802. If it has, then the routine passes to step 813 where the motor is turned on, the "motor3" flag is set, the "motor2" flag is cleared and a 0.5 second alarm is set, and thereafter the routine passes to process the new data at step 802. If at step 811 the "motor2" flag is not set, then the routine checks to see if the 0.5 second alarm has elapsed at step 814. If it has not, then the routine returns to step 802 for new data. If it has, then at step 815 the routine turns off the motor, clears the firing flag, clears the "motor3" flag, adjusts the shot counter (decreasing the number of remaining dosages for and/or increasing the number of doses delivered by, the given cassette 4), stores the record (e.g., peak flow rate and total exhaled volume or the flow rate and flow volume at drug delivery), and returns to obtain new data at step 802.

The selected time interval, for example, ½ second, provides sufficient time for trigger tip 313 to pass out of slot 234 and the release of torsion spring 220, to reload compression spring 210, and to refill the metered dose chamber of canister 31 following release of the medication. Although not shown in FIG. 19B, device 6 is turned off by rotating mouthpiece 20 so that contact switch 460 no longer engages location mark 44.

Advantageously, the press, controlled hold, and release behavior of the present invention provides for the internal metering chamber of metered dose canister 30 to be refilled shortly after releasing the dose of medication. This is important because the metering chamber must be refilled, i.e., the canister released, after the canister is agitated. Typically, the patient is instructed to agitate the medication prior to release of a dose, but that agitation is for filling the chamber for the next dose.

The precisely timed press and release behavior also ensures reproducible canister actuation. It also permits the use of canister nozzle combinations with a variety of emptying times because the emptying time parameter, i.e., the hold actuation time, is selectable and programmable. It should be understood that persons of ordinary skill in the art could develop considerably more complicated processes for sensing flow analyzing information and determining when to depress the canister to release a dose of aerosol medication. Such modifications are believed to be within the ability of a person of ordinary skill in the art.

All of the numbers and specific dimensions provided herein are exemplary. It is to be understood that the dimensions can be generally varied to obtain the desired release and flow characteristics, specifically different ranges of pressures in the two directions, as desired.

One skilled in the art will appreciate that the present invention can be practiced by other than the described embodiments, which are presented for purposes of illustration and not of limitation.

We claim:

1. A method of calibrating the output of a transducer in a flow path through which a medication is delivered from a hand-held metered dose inhaler, said transducer for sensing flow rates of human breath during inhalation and exhalation through a portion of a flow path in said inhaler, said flow rates having two non-linear flow characteristics and being in opposite directions therethrough over different ranges of flow, said flow path portion providing flow rate measurements representative of flow paths of the entire system, said method comprising:

(a) mounting a hand-held metered dose inhaler on a fixture terminating in a disposable cassette drug cassette;

(b) providing a flow controller having a controllable calibrated flow rate;

(c) selecting a first direction of flow simulating air flow during inhalation through the flow path and assigning a first plurality of data points defining a first flow rate range for the first direction, each of said first plurality of data points having a known flow rate;

(d) passing air at a first known flow rate into the flow path in a first direction and monitoring the signal output by the transducer in response to the first known flow rate;

(e) repeating step (d) for each other known flow rate in the first plurality of data points;

(f) deriving a first calibration array correlating the sensed transducer output with the corresponding known flow rate for each of the first plurality of data points;

(g) selecting a second direction of flow simulating flow rates during exhalation through the flow path and assigning a second plurality of data points defining a second flow rate range for the second direction, each of said second plurality of data points having a known flow rate;

(h) passing air at a second known flow rate into the flow path in the second direction and monitoring the signal output by the transducer in response to the second known flow rate;

(i) repeating step (h) for each other known flow rate in the second plurality of data points;

(j) deriving a second calibration array correlating the sensed transducer output with the known flow rate for each of the second plurality of data points;

(k) providing the first and second calibration arrays for determining the sensed flow in the first and second directions corresponding to inhalation and exhalation respectively;

(l) downloading the derived first and second calibration arrays into a memory device associated with the flow sensor;

(m) calculating a check sum for the downloaded first and second calibration arrays for determining whether or not the downloaded arrays are corrupted;

(n) testing the downloaded memory with one or more known flow rates to verify accuracy of the downloading step (l);

wherein steps (f) and (j) each further comprises processing the sensed transducer signals and correlated flow rates for each of the plurality of data points to identify outlying data points;

wherein the processing step further comprises repeating step (d) or (b) for each known flow rate identified as an outlying data point and thereafter further processing the sensed transducer signals and correlated known flow rates for each of the plurality of data points to identify any remaining outlying data points;

wherein steps (c) and (g) further comprise selecting the first and second pluralities of data points for human breath flow wherein the difference between the first and second ranges is selected from between a ratio of 2:5 to 1:100; and wherein selecting the first plurality of data points further comprises selecting a plurality of data points over a range of from 0 to 200 liters per minute corresponding to breath inhalation.

2. The method of claim 1 wherein the processing step further comprises applying a curve fitting routine to determine a transducer output signal corresponding to each known flow rate that is identified to be an outlying data point.

3. The method of claim 1 wherein the first plurality of data points is on the order of 30 known flow rates and the second plurality of data points is on the order of 30 known flow rates.

4. The method of claim 1 wherein selecting the second plurality of data points further comprises selecting a plurality of data points over the range of from 0 to 720 liters per minute corresponding to breath exhalation.

5. The method of claim 1 wherein steps (d)–(f) and (h)–(j) are performed automatically under computer control.

\* \* \* \* \*